(12) United States Patent
Muhsin

(10) Patent No.: US 12,042,245 B2
(45) Date of Patent: Jul. 23, 2024

(54) MEDICAL SYSTEMS AND METHODS

(71) Applicant: MASIMO CORPORATION, Irvine, CA (US)

(72) Inventor: Bilal Muhsin, Irvine, CA (US)

(73) Assignee: MASIMO CORPORATION, Irvine, CA (US)

( * ) Notice: Subject to any disclaimer, the term of this patent is extended or adjusted under 35 U.S.C. 154(b) by 0 days.

(21) Appl. No.: 18/045,359

(22) Filed: Oct. 10, 2022

(65) Prior Publication Data

US 2023/0233081 A1 Jul. 27, 2023

Related U.S. Application Data

(63) Continuation of application No. 16/601,464, filed on Oct. 14, 2019, now Pat. No. 11,464,410.

(60) Provisional application No. 62/745,244, filed on Oct. 12, 2018.

(51) Int. Cl.
*A61B 5/00* (2006.01)
*G06Q 10/1093* (2023.01)
*G16H 40/67* (2018.01)
*G16H 80/00* (2018.01)

(52) U.S. Cl.
CPC .......... *A61B 5/0022* (2013.01); *A61B 5/4833* (2013.01); *G06Q 10/1093* (2013.01); *G16H 40/67* (2018.01); *G16H 80/00* (2018.01)

(58) Field of Classification Search
CPC .... A61B 5/0022; A61B 5/4833; G16H 40/67; G16H 80/00; G16H 10/60; G16H 20/10; G06Q 10/1093; G06Q 10/06311
See application file for complete search history.

(56) References Cited

U.S. PATENT DOCUMENTS

| | | | |
|---|---|---|---|
| 4,960,128 | A | 10/1990 | Gordon et al. |
| 4,964,408 | A | 10/1990 | Hink et al. |
| 5,041,187 | A | 8/1991 | Hink et al. |

(Continued)

FOREIGN PATENT DOCUMENTS

| | | |
|---|---|---|
| JP | 2017-518834 | 7/2017 |
| WO | WO 2017/139761 | 8/2017 |

(Continued)

OTHER PUBLICATIONS

US 2022/0192529 A1, 06/2022, Al-Ali et al. (withdrawn)

(Continued)

*Primary Examiner* — Shirley X Jian
(74) *Attorney, Agent, or Firm* — Knobbe, Martens, Olson & Bear, LLP

(57) ABSTRACT

A medical system is disclosed. The medical system can include a patient monitoring device, a patient information system, and a mobile application. The patient monitoring device can be coupled to a patient to monitor one or more physiological parameters. The patient information system can allow the patient to communicate with a clinician. The patient information system can also provide information regarding schedules, medications, and procedures to the patient. The mobile application can be communicatively coupled with the patient monitoring device and the patient information system. The mobile application can allow a clinician to receive, view, and send information to or from the patient monitoring device and the patient information system.

17 Claims, 24 Drawing Sheets

(56) References Cited

U.S. PATENT DOCUMENTS

| | | |
|---|---|---|
| 5,069,213 A | 12/1991 | Hink et al. |
| 5,163,438 A | 11/1992 | Gordon et al. |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| 5,441,047 A | 8/1995 | David et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,544,649 A | 8/1996 | David et al. |
| 5,561,275 A | 10/1996 | Savage et al. |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,685,299 A | 11/1997 | Diab et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,673 A | 9/2000 | Malin et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,163,281 A | 12/2000 | Torch |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,611,206 B2 | 8/2003 | Eshelman et al. |
| 6,611,707 B1 | 8/2003 | Prausnitz et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |

(56) References Cited

U.S. PATENT DOCUMENTS

| | | |
|---|---|---|
| 6,721,585 B1 | 4/2004 | Parker |
| 6,723,046 B2 | 4/2004 | Lichtenstein |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,767,341 B2 | 7/2004 | Cho |
| 6,770,028 B1 | 8/2004 | Ali et al. |
| 6,771,994 B2 | 8/2004 | Kiani et al. |
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,936,007 B2 | 8/2005 | Quy |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,976,958 B2 | 12/2005 | Quy |
| 6,979,812 B2 | 12/2005 | Al-Ali |
| 6,985,524 B1 | 1/2006 | Borchers |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,142,901 B2 | 11/2006 | Kiani et al. |
| 7,149,561 B2 | 12/2006 | Diab |
| 7,156,809 B2 | 1/2007 | Quy |
| 7,186,966 B2 | 3/2007 | Al-Ali |
| 7,190,261 B2 | 3/2007 | Al-Ali |
| 7,215,984 B2 | 5/2007 | Diab et al. |
| 7,215,986 B2 | 5/2007 | Diab et al. |
| 7,220,000 B2 | 5/2007 | Alster et al. |
| 7,221,971 B2 | 5/2007 | Diab et al. |
| 7,225,006 B2 | 5/2007 | Al-Ali et al. |
| 7,225,007 B2 | 5/2007 | Al-Ali et al. |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali et al. |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali et al. |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty et al. |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,733,224 B2 | 6/2010 | Tran |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |

(56) References Cited

U.S. PATENT DOCUMENTS

| | | |
|---|---|---|
| 7,801,581 B2 | 9/2010 | Diab |
| 7,822,452 B2 | 10/2010 | Schurman et al. |
| RE41,912 E | 11/2010 | Parker |
| 7,839,266 B2 | 11/2010 | Hoglund et al. |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 7,999,685 B2 | 8/2011 | Sanchez et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,135,227 B2 | 3/2012 | Lewis et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,390,694 B2 | 3/2013 | Ryan et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellott et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,591,430 B2 | 11/2013 | Amurthur et al. |
| 8,600,467 B2 | 12/2013 | Al-Ali et al. |
| 8,603,384 B2 | 12/2013 | Luttge et al. |
| 8,606,342 B2 | 12/2013 | Diab |
| 8,615,408 B2 | 12/2013 | Ryan |
| 8,622,922 B2 | 1/2014 | Banet et al. |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |

(56) References Cited

U.S. PATENT DOCUMENTS

| | | | |
|---|---|---|---|
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,810,408 B2 * | 8/2014 | Hanson .................. G16H 20/13 |
| | | 128/200.14 |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,956,287 B2 * | 2/2015 | Zdeblick ................ G16H 20/10 |
| | | 424/9.1 |
| 8,965,471 B2 | 2/2015 | Lamego |
| 8,968,195 B2 | 3/2015 | Tran |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,075 B2 | 11/2015 | Baker, Jr. et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,283,150 B2 | 3/2016 | Bujalski et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-Ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,405,135 B2 | 8/2016 | Sweis et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,495,881 B2 * | 11/2016 | Christmas ............... G06F 3/048 |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,706 B2 | 1/2017 | Soomro et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |

(56) References Cited

U.S. PATENT DOCUMENTS

| | | |
|---|---|---|
| 9,579,039 B2 | 2/2017 | Jansen et al. |
| 9,591,975 B2 | 3/2017 | Dalvi et al. |
| 9,597,004 B2 | 3/2017 | Hughes et al. |
| 9,615,792 B2 | 4/2017 | Raptis et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,700,222 B2 | 7/2017 | Quinlan et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,820,699 B2 | 11/2017 | Bingley et al. |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,887,650 B2 | 2/2018 | Maekawa et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali et al. |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| 10,008,091 B2 | 6/2018 | Mason et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,445 B1 | 8/2018 | Torch |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,726 B2 | 11/2018 | Al-Ali et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Kiani et al. |
| 10,188,348 B2 | 1/2019 | Al-Ali et al. |
| RE47,218 E | 2/2019 | Al-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B1 | 5/2019 | Poeze et al. |
| 10,299,709 B2 | 5/2019 | Perea et al. |
| 10,299,720 B2 | 5/2019 | Brown et al. |
| 10,305,775 B2 | 5/2019 | Lamego et al. |
| 10,307,111 B2 | 6/2019 | Muhsin et al. |
| 10,325,681 B2 | 6/2019 | Sampath et al. |
| 10,327,337 B2 | 6/2019 | Schmidt et al. |
| 10,327,713 B2 | 6/2019 | Barker et al. |

(56) References Cited

U.S. PATENT DOCUMENTS

| | | |
|---|---|---|
| 10,332,623 B2 | 6/2019 | Edwards et al. |
| 10,332,630 B2 | 6/2019 | Al-Ali |
| 10,335,033 B2 | 7/2019 | Al-Ali |
| 10,335,068 B2 | 7/2019 | Poeze et al. |
| 10,335,072 B2 | 7/2019 | Al-Ali et al. |
| 10,339,500 B2 | 7/2019 | Hussam |
| 10,342,470 B2 | 7/2019 | Al-Ali et al. |
| 10,342,487 B2 | 7/2019 | Al-Ali et al. |
| 10,342,497 B2 | 7/2019 | Al-Ali et al. |
| 10,349,895 B2 | 7/2019 | Telfort et al. |
| 10,349,898 B2 | 7/2019 | Al-Ali et al. |
| 10,354,504 B2 | 7/2019 | Kiani et al. |
| 10,357,206 B2 | 7/2019 | Weber et al. |
| 10,357,209 B2 | 7/2019 | Al-Ali |
| 10,366,787 B2 | 7/2019 | Sampath et al. |
| 10,368,787 B2 | 8/2019 | Reichgott et al. |
| 10,376,190 B1 | 8/2019 | Poeze et al. |
| 10,376,191 B1 | 8/2019 | Poeze et al. |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| 10,398,320 B2 | 9/2019 | Kiani et al. |
| 10,405,804 B2 | 9/2019 | Al-Ali |
| 10,413,666 B2 | 9/2019 | Al-Ali et al. |
| 10,420,493 B2 | 9/2019 | Al-Ali et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| 10,691,777 B2 * | 6/2020 | Dettinger ............... G16H 70/20 |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf et al. |
| D906,970 S | 1/2021 | Forrest et al. |
| 10,916,336 B2 | 2/2021 | Fiedler et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| D946,596 S | 3/2022 | Ahmed |
| D946,597 S | 3/2022 | Ahmed |
| D946,598 S | 3/2022 | Ahmed |
| D946,617 S | 3/2022 | Ahmed |
| 11,272,839 B2 | 3/2022 | Al-Ali et al. |
| 11,285,121 B2 | 3/2022 | Chang et al. |
| 11,289,199 B2 | 3/2022 | Al-Ali |
| RE49,034 E | 4/2022 | Al-Ali |
| 11,298,021 B2 | 4/2022 | Muhsin et al. |
| D950,580 S | 5/2022 | Ahmed |
| D950,599 S | 5/2022 | Ahmed |
| D957,648 S | 7/2022 | Al-Ali |
| 11,389,093 B2 | 7/2022 | Triman et al. |
| 11,406,286 B2 | 8/2022 | Al-Ali et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0022973 A1 | 2/2002 | Sun et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2004/0106858 A1 | 6/2004 | Say et al. |
| 2005/0055276 A1 | 3/2005 | Kiani et al. |
| 2005/0227929 A1 | 10/2005 | Masferrer |
| 2005/0234317 A1 | 10/2005 | Kiani |
| 2005/0240444 A1 * | 10/2005 | Wooten .................. G06Q 30/02 705/3 |
| 2006/0073719 A1 | 4/2006 | Kiani |
| 2006/0140502 A1 | 6/2006 | Tseng et al. |
| 2006/0161054 A1 | 7/2006 | Reuss et al. |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2007/0282478 A1 | 12/2007 | Al-Ali et al. |
| 2007/0293781 A1 | 12/2007 | Sims et al. |
| 2007/0299694 A1 | 12/2007 | Merck |
| 2008/0008745 A1 | 1/2008 | Stinchcomb et al. |
| 2008/0064965 A1 | 3/2008 | Jay et al. |
| 2008/0094228 A1 | 4/2008 | Welch et al. |
| 2008/0097795 A1 | 4/2008 | Sasai et al. |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0094220 A1 | 4/2010 | Mandro |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0054924 A1 | 3/2011 | Mitchell et al. |
| 2011/0082711 A1 | 4/2011 | Poeze et al. |
| 2011/0087081 A1 | 4/2011 | Kiani et al. |

(56) References Cited

U.S. PATENT DOCUMENTS

| | | |
|---|---|---|
| 2011/0118561 A1 | 5/2011 | Tari et al. |
| 2011/0125060 A1 | 5/2011 | Telfort et al. |
| 2011/0137297 A1 | 6/2011 | Kiani et al. |
| 2011/0137680 A1 | 6/2011 | Sweeney |
| 2011/0172498 A1 | 7/2011 | Olsen et al. |
| 2011/0208015 A1 | 8/2011 | Welch et al. |
| 2011/0230733 A1 | 9/2011 | Al-Ali |
| 2012/0041279 A1 | 2/2012 | Freeman et al. |
| 2012/0084101 A1* | 4/2012 | Qadri ............... G16H 10/60 705/3 |
| 2012/0101847 A1 | 4/2012 | Johnson et al. |
| 2012/0123231 A1 | 5/2012 | O'Reilly |
| 2012/0136232 A1 | 5/2012 | Jeong et al. |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0033485 A1 | 2/2013 | Kollin et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0096819 A1 | 4/2013 | Tarnok |
| 2013/0096936 A1 | 4/2013 | Sampath et al. |
| 2013/0172759 A1 | 7/2013 | Melker et al. |
| 2013/0218588 A1* | 8/2013 | Kehr ............... G16H 40/63 705/2 |
| 2013/0243021 A1 | 9/2013 | Siskavich |
| 2013/0253334 A1 | 9/2013 | Al-Ali et al. |
| 2013/0296672 A1 | 11/2013 | O'Neil et al. |
| 2013/0296713 A1 | 11/2013 | Al-Ali et al. |
| 2013/0324808 A1 | 12/2013 | Al-Ali et al. |
| 2013/0331660 A1 | 12/2013 | Al-Ali et al. |
| 2013/0345921 A1 | 12/2013 | Al-Ali et al. |
| 2014/0012100 A1 | 1/2014 | Al-Ali et al. |
| 2014/0051953 A1 | 2/2014 | Lamego et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0163344 A1 | 6/2014 | Al-Ali |
| 2014/0164022 A1 | 6/2014 | Reed et al. |
| 2014/0166076 A1 | 6/2014 | Kiani et al. |
| 2014/0171763 A1 | 6/2014 | Diab |
| 2014/0173674 A1 | 6/2014 | Wolman et al. |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0228657 A1 | 8/2014 | Palley et al. |
| 2014/0257852 A1 | 9/2014 | Walker et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0278536 A1 | 9/2014 | Zhang et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0350966 A1 | 11/2014 | Khatana et al. |
| 2014/0357966 A1 | 12/2014 | Al-Ali et al. |
| 2014/0376789 A1 | 12/2014 | Xu et al. |
| 2015/0005600 A1 | 1/2015 | Blank et al. |
| 2015/0011907 A1 | 1/2015 | Purdon et al. |
| 2015/0032029 A1 | 1/2015 | Al-Ali et al. |
| 2015/0038859 A1 | 2/2015 | Dalvi et al. |
| 2015/0050633 A1* | 2/2015 | Christmas ............. G06F 3/0486 715/762 |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0099950 A1 | 4/2015 | Al-Ali et al. |
| 2015/0100343 A1* | 4/2015 | Siedlecki ............... G16H 20/10 705/2 |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0134107 A1 | 5/2015 | Hyde et al. |
| 2015/0134345 A1 | 5/2015 | Hyde et al. |
| 2015/0141910 A1 | 5/2015 | Francis et al. |
| 2015/0165312 A1 | 6/2015 | Kiani |
| 2015/0173674 A1 | 6/2015 | Hayes et al. |
| 2015/0196249 A1 | 7/2015 | Brown et al. |
| 2015/0216459 A1 | 8/2015 | Al-Ali et al. |
| 2015/0238722 A1 | 8/2015 | Al-Ali |
| 2015/0244878 A1 | 8/2015 | Macauley et al. |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0317891 A1 | 11/2015 | Day et al. |
| 2015/0351697 A1 | 12/2015 | Weber et al. |
| 2015/0359429 A1 | 12/2015 | Al-Ali et al. |
| 2015/0366507 A1 | 12/2015 | Blank et al. |
| 2015/0367071 A1 | 12/2015 | Donnellan et al. |
| 2016/0019360 A1 | 1/2016 | Pahwa et al. |
| 2016/0029932 A1 | 2/2016 | Al-Ali |
| 2016/0058347 A1 | 3/2016 | Reichgott et al. |
| 2016/0066824 A1 | 3/2016 | Al-Ali et al. |
| 2016/0071392 A1 | 3/2016 | Hankey et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0098536 A1* | 4/2016 | Dettinger ................ G09B 5/02 705/2 |
| 2016/0103598 A1 | 4/2016 | Al-Ali et al. |
| 2016/0129182 A1 | 5/2016 | Schuster et al. |
| 2016/0166182 A1 | 6/2016 | Al-Ali et al. |
| 2016/0166183 A1 | 6/2016 | Poeze et al. |
| 2016/0166766 A1 | 6/2016 | Schuster et al. |
| 2016/0189317 A1 | 6/2016 | Papandrea |
| 2016/0196388 A1 | 7/2016 | Lamego |
| 2016/0197436 A1 | 7/2016 | Barker et al. |
| 2016/0212404 A1 | 7/2016 | Maiello et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0263317 A1 | 9/2016 | Arefieg |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324488 A1 | 11/2016 | Olsen |
| 2016/0327984 A1 | 11/2016 | Al-Ali et al. |
| 2016/0328993 A1 | 11/2016 | Brogioli |
| 2016/0331332 A1 | 11/2016 | Al-Ali |
| 2016/0367173 A1 | 12/2016 | Dalvi et al. |
| 2016/0371833 A1 | 12/2016 | Prasad et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali |
| 2017/0079594 A1 | 3/2017 | Telfort et al. |
| 2017/0084133 A1 | 3/2017 | Cardinali et al. |
| 2017/0086723 A1 | 3/2017 | Al-Ali et al. |
| 2017/0094450 A1 | 3/2017 | Tu et al. |

(56) References Cited

U.S. PATENT DOCUMENTS

| | | |
|---|---|---|
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0172522 A1 | 6/2017 | Insler et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0246390 A1 | 8/2017 | Tchao et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0262604 A1 | 9/2017 | Francois |
| 2017/0287316 A1 | 10/2017 | Wildman et al. |
| 2017/0293727 A1 | 10/2017 | Klaassen et al. |
| 2017/0311851 A1 | 11/2017 | Schurman et al. |
| 2017/0311891 A1 | 11/2017 | Kiani et al. |
| 2017/0325728 A1 | 11/2017 | Al-Ali et al. |
| 2017/0332952 A1 | 11/2017 | Desborough et al. |
| 2017/0332976 A1 | 11/2017 | Al-Ali |
| 2017/0340293 A1 | 11/2017 | Al-Ali et al. |
| 2017/0358242 A1 | 12/2017 | Thompson et al. |
| 2017/0360310 A1 | 12/2017 | Kiani |
| 2017/0366627 A1 | 12/2017 | Chan et al. |
| 2017/0367632 A1 | 12/2017 | Al-Ali et al. |
| 2017/0372018 A1 | 12/2017 | Rosenblatt et al. |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0028124 A1 | 2/2018 | Al-Ali et al. |
| 2018/0035101 A1 | 2/2018 | Osterhout |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0098698 A1 | 4/2018 | Marcus et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0110923 A1 | 4/2018 | Kaplan et al. |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0137932 A1 | 5/2018 | Fiedler et al. |
| 2018/0146901 A1 | 5/2018 | Al-Ali et al. |
| 2018/0146902 A1 | 5/2018 | Kiani et al. |
| 2018/0147343 A1 | 5/2018 | Tyson |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174261 A1 | 6/2018 | Brabazon |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0200433 A1 | 7/2018 | Cirit |
| 2018/0206733 A1 | 7/2018 | Kasan et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0264242 A1 | 9/2018 | Hoffman et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin et al. |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |
| 2019/0038143 A1 | 2/2019 | Al-Ali |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0076028 A1 | 3/2019 | Al-Ali et al. |
| 2019/0082979 A1 | 3/2019 | Al-Ali et al. |
| 2019/0090748 A1 | 3/2019 | Al-Ali |
| 2019/0090760 A1 | 3/2019 | Kinast et al. |
| 2019/0090764 A1 | 3/2019 | Al-Ali |
| 2019/0104973 A1 | 4/2019 | Poeze et al. |
| 2019/0110719 A1 | 4/2019 | Poeze et al. |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Al-Ali |
| 2019/0122763 A1 | 4/2019 | Sampath et al. |
| 2019/0133525 A1 | 5/2019 | Al-Ali et al. |
| 2019/0142283 A1 | 5/2019 | Lamego et al. |
| 2019/0142344 A1 | 5/2019 | Telfort et al. |
| 2019/0150800 A1 | 5/2019 | Poeze et al. |
| 2019/0150856 A1 | 5/2019 | Kiani et al. |
| 2019/0167161 A1 | 6/2019 | Al-Ali et al. |
| 2019/0175019 A1 | 6/2019 | Al-Ali et al. |
| 2019/0192076 A1 | 6/2019 | McHale et al. |
| 2019/0200941 A1 | 7/2019 | Chandran et al. |
| 2019/0201623 A1 | 7/2019 | Kiani |
| 2019/0209025 A1 | 7/2019 | Ai-Ali |
| 2019/0209084 A1 | 7/2019 | Bryant et al. |
| 2019/0214778 A1 | 7/2019 | Scruggs et al. |
| 2019/0216317 A1 | 7/2019 | Grande |
| 2019/0216319 A1 | 7/2019 | Poeze et al. |
| 2019/0216321 A1 | 7/2019 | Grande |
| 2019/0216379 A1 | 7/2019 | Al-Ali et al. |
| 2019/0221320 A1 | 7/2019 | Amini et al. |
| 2019/0221966 A1 | 7/2019 | Kiani et al. |
| 2019/0223804 A1 | 7/2019 | Blank et al. |
| 2019/0231199 A1 | 8/2019 | Al-Ali et al. |
| 2019/0231241 A1 | 8/2019 | Al-Ali et al. |

(56) References Cited

U.S. PATENT DOCUMENTS

| | | |
|---|---|---|
| 2019/0231270 A1 | 8/2019 | Abdul-Hafiz et al. |
| 2019/0239787 A1 | 8/2019 | Pauley et al. |
| 2019/0239824 A1 | 8/2019 | Muhsin et al. |
| 2019/0254578 A1 | 8/2019 | Lamego |
| 2019/0261857 A1 | 8/2019 | Al-Ali |
| 2019/0269370 A1 | 9/2019 | Al-Ali et al. |
| 2019/0274606 A1 | 9/2019 | Kiani et al. |
| 2019/0274627 A1 | 9/2019 | Al-Ali et al. |
| 2019/0274635 A1 | 9/2019 | Al-Ali et al. |
| 2019/0290136 A1 | 9/2019 | Dalvi et al. |
| 2019/0298270 A1 | 10/2019 | Al-Ali et al. |
| 2019/0304601 A1 | 10/2019 | Sampath et al. |
| 2019/0304605 A1 | 10/2019 | Al-Ali |
| 2019/0320906 A1 | 10/2019 | Olsen |
| 2019/0336085 A1 | 11/2019 | Kayser et al. |
| 2019/0365315 A1 | 12/2019 | Ramabadran |
| 2019/0374713 A1 | 12/2019 | Kiani et al. |
| 2020/0054250 A1 | 2/2020 | Joseph et al. |
| 2020/0054278 A1 | 2/2020 | Joseph et al. |
| 2020/0060869 A1 | 2/2020 | Telfort et al. |
| 2020/0066415 A1 | 2/2020 | Hettig et al. |
| 2020/0101166 A1 | 4/2020 | Jenkins et al. |
| 2020/0111552 A1 | 4/2020 | Ahmed |
| 2020/0113488 A1 | 4/2020 | Al-Ali et al. |
| 2020/0113496 A1 | 4/2020 | Scruggs et al. |
| 2020/0113497 A1 | 4/2020 | Triman et al. |
| 2020/0113520 A1 | 4/2020 | Abdul-Hafiz et al. |
| 2020/0129117 A1 | 4/2020 | Henderson |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0262864 A1 | 8/2020 | Barbut et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0020307 A1 | 1/2021 | Bhimavarapu et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0247393 A1 | 8/2021 | Chorny et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0345974 A1 | 11/2021 | Chung |
| 2021/0386382 A1 | 12/2021 | Olsen et al. |
| 2021/0398667 A1 | 12/2021 | Fujioka |
| 2021/0402110 A1 | 12/2021 | Pauley et al. |
| 2022/0026355 A1 | 1/2022 | Normand et al. |
| 2022/0039707 A1 | 2/2022 | Sharma et al. |
| 2022/0053892 A1 | 2/2022 | Al-Ali et al. |
| 2022/0071562 A1 | 3/2022 | Kiani |
| 2022/0096603 A1 | 3/2022 | Kiani et al. |
| 2022/0105289 A1 | 4/2022 | Lancaster |
| 2022/0151521 A1 | 5/2022 | Krishnamani et al. |
| 2022/0218244 A1 | 7/2022 | Kiani et al. |

FOREIGN PATENT DOCUMENTS

| | | |
|---|---|---|
| WO | WO 2018/065284 | 4/2018 |
| WO | WO 2018/094520 | 5/2018 |
| WO | WO 2018/110510 | 6/2018 |
| WO | WO 2018/020911 | 7/2018 |
| WO | WO 2019/236759 | 12/2019 |
| WO | WO 2021/189007 | 9/2021 |

OTHER PUBLICATIONS

A "Second Chance" to Prevent Opioid Deaths, Technology Networks, Informatics News, This App Uses Sonar to Detect Opioid Overdoses, University of Washington, Jan. 10, 2019, in 3 pages, https://www.technologynetworks.com/informatics/news/a-second-chance-to-prevent-opioid-deaths-313744.

Announcing the Winner of the 2016 FDA Naloxone APP Competition, U.S. Food & Drug Administration, dated 2016, in 2 pages. https://www.fda.gov/news-events/public-health-focus/announcing-winner-2016-fda-naloxone-app-competition.

Blair, Andre, Monitoring for Opioid Overdoses: HopeBand Can Save People's Life, Advocator, dated Dec. 28, 2018 in 2 pages. https://advocator.ca/news/monitoring-for-opioid-overdoses-hopeband-can-save-peoples-life.

England, Rachel, "Wearable Sensor Can Detect Imminent Opioid Overdose, the low-cost device gives wearers the opportunity to administer life-saving drugs", Engadget, https://www.engadget.com/2018/12/28/wearable-sensor-opioid-overdose/?guccounter=1, Dec. 28, 2018, in 3 pages.

Hsu, Jeremy, Wristband That Detects Opioid Overdose Joins U.S. Race for Tech Solutions, IEEE Spectrum's Biomedical Engineering Blog, dated Dec. 26, 2018, in 2 pages.

International Search Report and Written Opinion received in PCT Application No. PCT/US2019/035664, dated Nov. 6, 2019 in 17 pages.

International Search Report and Written Opinion received in PCT Application No. PCT/US2021/023336, dated Jun. 25, 2021 in 12 pages.

McKibben, Justin, OD Help App Could Make Getting Naloxone Like Getting an Uber, Palm Partners Drug Rehab Center, 2018, in 7 pages. https://www.palmpartners.com/od-help-app-naloxone-uber/.

Middlebrook, Hailey, OD Help app wins FDA's competition to help fight heroin overdose, CNN, dated Dec. 19, 2016, in 4 pages. http://www.cnn.com/2016/09/22/health/fda-heroin-app-competition/index.html.

Muoio, Dave, "Robert Wood Johnson Foundation Names Winners of $50,000 AI, Opioid Challenges", Mobihealthnews, dated Sep. 19, 2018, in 13 pages. https://www.mobihealthnews.com/content/robert-wood-johnson-foundation-names-winners-50000-ai-opioid-challenges.

Nandakumar et al., "Opioid Overdose Detection Using Smartphones", Science Translational Medicine, vol. 11, No. 474, Research Article, Jan. 9, 2019, pp. 10.

Opioid Overdose, SAMHSA-Substance Abuse and Mental Health Services Administration, retrieved Jul. 2, 2019, in 2 pages. http://www.samhsa.gov/medication-assisted-treatment/treatment/opioid-overdose.

"OD Help", PwrdBy, published Nov. 7, 2016, https://www.youtube.com/watch?v=wiiNvSLbUgo in 1 page.

Singer, "Pill dispenser that's set by timer may stop opioid addiction before it starts" https://www.democratandchronicle.com, May 8, 2018, in 6 pages.

Young, Grace, "NALNOW—2016 FDA Naloxone App Competition", Nov. 7, 2016, retrieved from https://www.youtube.com/watch?v=DKsHBJm9uNc&feature=youtu.be.

* cited by examiner

FIG. 9

MEDICAL SYSTEMS AND METHODS

INCORPORATION BY REFERENCE TO ANY PRIORITY APPLICATIONS

This application is a continuation of U.S. patent application Ser. No. 16/601,464, filed Oct. 14, 2019, and entitled "MEDICAL SYSTEMS AND METHODS," which claims priority to U.S. Provisional Patent Application 62/745,244, filed Oct. 12, 2018, and entitled "MEDICAL SYSTEMS AND METHODS." These and any other applications for which a foreign or domestic priority claim is identified in the Application Data Sheet as filed with the present application are hereby incorporated by reference under 37 CFR 1.57.

BACKGROUND

Field

This disclosure relates to systems, devices, and methods with applications in, for example, hospitals and other patient care facilities.

Description of the Related Art

Hospitals, nursing homes, and other patient care facilities typically include patient monitoring devices at one or more bedsides in the facility. Patient monitoring devices generally include sensors, processing equipment, and displays for obtaining and analyzing a medical patient's physiological parameters. Physiological parameters include, for example, respiratory rate, $SpO_2$ level, pulse, and blood pressure, among others. Clinicians, including doctors, nurses, and certain other medical personnel use the physiological parameters obtained from the medical patient to diagnose illnesses and to prescribe treatments. Clinicians also use the physiological parameters to monitor a patient during various clinical situations to determine whether to increase the level of medical care given to the patient.

Patient monitors capable of measuring pulse oximetry parameters, such as SpO2 and pulse rate in addition to advanced parameters, such as HbCO, HbMet and total hemoglobin (Hbt) and corresponding multiple wavelength optical sensors are described in at least U.S. patent application Ser. No. 11/367,013, filed Mar. 1, 2006 and entitled Multiple Wavelength Sensor Emitters and U.S. patent application Ser. No. 11/366,208, filed Mar. 1, 2006 and entitled Noninvasive Multi-Parameter Patient Monitor, both assigned to Masimo Laboratories, Irvine, CA (Masimo Labs) and both incorporated by reference herein. Further, noninvasive blood parameter monitors and corresponding multiple wavelength optical sensors, such as Rainbow™ adhesive and reusable sensors and RAD-57™ and Radical-7™ monitors for measuring SpO2, pulse rate, perfusion index, signal quality, HbCO and HbMet among other parameters are also available from Masimo Corporation, Irvine, CA (Masimo).

Advanced physiological monitoring systems may incorporate pulse oximetry in addition to advanced features for the calculation and display of other blood parameters, such as carboxyhemoglobin (HbCO), methemoglobin (HbMet) and total hemoglobin (Hbt), as a few examples. Advanced physiological monitors and corresponding multiple wavelength optical sensors capable of measuring parameters in addition to SpO2, such as HbCO, HbMet and Hbt are described in at least U.S. patent application Ser. No. 11/367,013, filed Mar. 1, 2006, titled Multiple Wavelength Sensor Emitters and U.S. patent application Ser. No. 11/366,208, filed Mar. 1, 2006, titled Noninvasive Multi-Parameter Patient Monitor, assigned to Masimo Labs and incorporated by reference herein. Further, noninvasive blood parameter monitors and corresponding multiple wavelength optical sensors, such as Rainbow™ adhesive and reusable sensors and RAD-57™ and Radical-7™ monitors for measuring SpO2, pulse rate, perfusion index (PI), signal quality (SiQ), pulse variability index (PVI), HbCO and HbMet among other parameters are also available from Masimo.

SUMMARY

A medical system is disclosed. The medical system can include a patient monitoring device, a patient information system, and a mobile application. The patient monitoring device can be coupled to a patient to monitor one or more physiological parameters. The patient information system can allow the patient to communicate with a clinician. The patient information system can also provide information regarding schedules, medications, and procedures to the patient. The mobile application can be communicatively coupled with the patient monitoring device and the patient information system. The mobile application can allow a clinician to receive, view, and send information to or from the patient monitoring device and the patient information system.

BRIEF DESCRIPTION OF THE DRAWINGS

Various embodiments will be described hereinafter with reference to the accompanying drawings. These embodiments are illustrated and described by example only, and are not intended to limit the scope of the disclosure.

FIG. 9 is a screen shot of an example user interface for monitoring patients in the clinical network environment of FIG. 6;

DETAILED DESCRIPTION

A physiological monitoring system of certain embodiments includes one or more patient monitoring devices connected to a shared network using open architecture communications standards. The patient monitoring devices of certain embodiments include a physiological monitor coupled with a network interface module. The physiological monitor includes one or more sensors and a sensor processing module for processing signals from the sensors. The network interface module receives physiological information from the sensor processing module and transmits this information over the shared network. The network interface module may connect to a variety of physiological monitors. In addition, the network interface module of various implementations is a portable bedside device assigned exclusively to one medical patient.

In certain embodiments, the network interface module facilitates establishing a network connection directly with end users over the shared network. These end users, including doctors, nurses, and other hospital staff, may receive physiological information, alarms, and alerts from the network interface module on an electronic device, such as a pager, PDA, laptop, computer, computer on wheels (COW), or the like.

Figure 1:
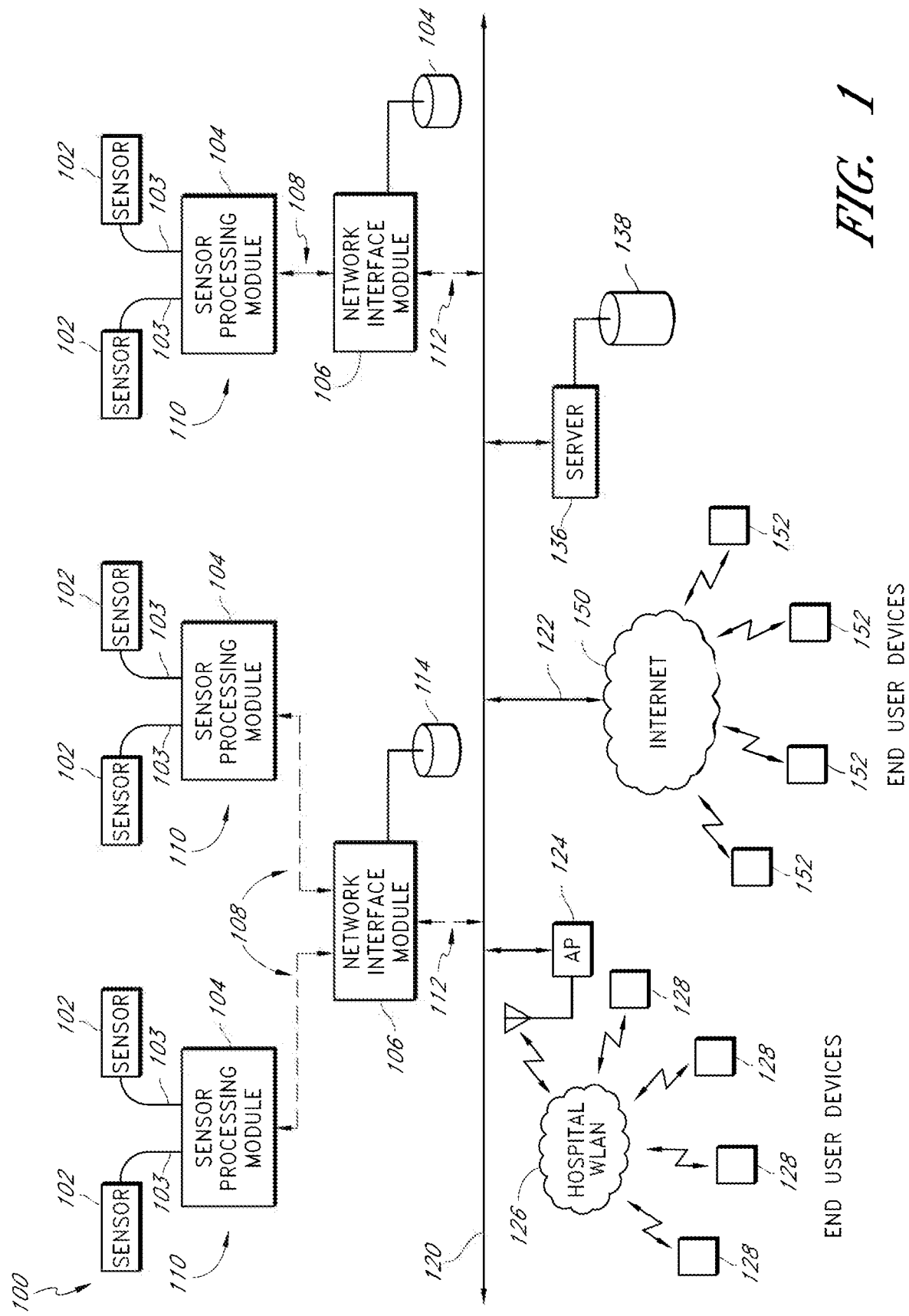
FIG. 1 is an example block diagram showing a physiological monitoring system according to some embodiments.

Referring to FIG. 1, certain embodiments of a physiological monitoring system 100 (e.g., alarm notification system) include an open network architecture using "off-the-shelf" hardware and communication protocols. This architecture in various implementations is a shared, or open, network includes multiple patient monitoring devices 110, a network bus 120 (e.g., an Ethernet backbone), and a hospital WLAN 126. In addition, the shared network may further include a connection 122 to the Internet 150, to end user devices 152 over the Internet 150, and to end user devices 128 over the hospital WLAN 126. The physiological monitoring system 100 of certain embodiments is therefore an enterprise system that achieves a cost-effective replacement for currently available patient monitoring systems.

The physiological monitoring system 100 includes a plurality of bedside devices, e.g., patient monitoring devices 110. The patient monitoring devices 110 of various embodiments include sensors 102, one or more sensor processing modules 104, and a communications module, e.g., network interface module 106. In the depicted embodiment, two patient monitoring devices 110 are shown. One patient monitoring device includes one set of sensors 102, one sensor processing module 104, and one network interface module 106. The other patient monitoring device 110 includes two sets of sensors 102, two sensor processing modules 104, and one network interface module 106.

In certain embodiments, each patient monitoring device 110 is used by one medical patient. The patient monitoring devices 110 form a network of patient monitoring devices 110, each of which can communicate with clinicians and other end users over a shared network, including a hospital network 126 and network interfaces to the Internet 150.

One or more sensors 102 of the patient monitoring device 110 are attached to a medical patient. These sensors 102 may include ECG sensors, acoustic sensors, pulse oximeters, and other types of sensors. The sensors 102 obtain physiological information from a medical patient and transmit this information to the sensor processing module 104 through cables 103 or through a wireless connection (not shown). In certain embodiments, the physiological information includes one or more physiological parameters or values and waveforms corresponding to the physiological parameters.

The sensor processing module 104 receives physiological information from the sensors 102. The sensor processing module 104 of certain embodiments includes a circuit having a processor, input ports for receiving the physiological information, software for processing the physiological information in the processor, an optional display, and optionally an input device (e.g., a keyboard). In addition, the sensor processing module 104 contains one or more output ports, such as serial ports. For example, an RS232, RS423, or autobaud RS232 (serial interface standard) port or a universal serial bus (USB) port may be included in the sensor processing module 104.

In certain embodiments, the sensor processing module 104 generates waveforms from signals received from the sensors 102. The sensor processing module 104 may also analyze single or multiparameter trends to provide early warning alerts to clinicians prior to an alarm event. In addition, the sensor processing module 104 in certain embodiments generates alarms in response to physiological parameters exceeding certain safe thresholds.

Example alerts include no communication with pulse oximeter, alarm silenced on pulse oximeter, instrument low battery (pulse oximeter), and transmitter low battery. Example alarms include $SpO_2$ levels and alarms, high and low $SpO_2$, high and low PR, HbCO level and alarms, HbMET level and alarms, pulse rate and alarms, no sensor, sensor off patient, sensor error, low perfusion index, low signal quality, HbCO, HbMET, PI trend alarm, and desat index alarm.

The network interface module 106 in the depicted embodiment is connected to one or more sensor processing modules 104 through one or more connectors 108, which may be serial connectors corresponding to the serial ports in the sensor processing modules 104. Dashed lines on the connector 108 indicate that the network interface module 106 of certain embodiments is not permanently attached to the sensor processing modules 104. In alternative embodiments (not shown), however, the network interface module 106 is contained within a sensor processing module 104.

The network interface module 106 in various implementations includes a processor, an input port (such as a standard RS232 serial port), a network output port such as an Ethernet port, and software which enables the network interface module 106 to act as a network-communications enabled device. In addition, the network interface module 106 includes a storage device 114, which may be included within the network interface module 106 or attached separately to the network interface module 106.

The network interface module 106 manages the connectivity overhead for initiating and maintaining connectivity with end user devices over the shared network. In certain embodiments, the network interface module 106 manages connectivity by acting as a microserver or web server. In such instances, the network interface module 106 is a network connection enabled device. As a web server, the network interface module 106 establishes direct connections to the Internet 150, such that an end user may access web pages stored on the storage device 114 of the network interface module 106. In one embodiment, the network interface module 106 therefore does not require a separate server for connecting to the Internet 150. In one embodiment, the network interface module 106 connects to the Internet 150 directly through a modem, such that the connection 122 includes a modem. In managing connectivity over the shared network, the network interface module 106 may also perform security management functions, such as user authentication.

In certain embodiments, the network interface module 106 sends data over the shared network through an access point 124 or other wireless or wired transmitter. Alternatively, the network interface module 106 may communicate physiological information directly to end users over the Internet 150. End users such as clinicians carrying notifier devices, e.g., end user devices 128, 152 connected to the hospital WLAN 126 may receive real-time viewing of physiological patient parameters and waveforms on demand or in the event of an alarm or alert. Real-time or slightly delayed transmission of physiological information in certain embodiments comports with standards for alarm latency in compliance with Joint Commission on Accreditation of Healthcare Organizations (JCAHO) standards for effective alarm response. The network interface module 106 of certain embodiments therefore adds functionality equivalent to a central nurses' station.

In certain embodiments, the network interface module 106 performs context management. In one embodiment, context management includes associating context information with physiological information to form a contextual data package. Context information may include several categories of information, including the categories of context information related to the network interface module 106, context information related to the medical patient, context information related to usage of the network interface module 106, and context information related to a network connection. Within one or more of these context categories, context information might include a patient name, a patients' unique hospital identification number, patient location, an identification number for a network interface module 106, time stamps for events occurring in the physiological monitoring system 100, environmental conditions such as changes to the state of the network and usage statistics of the network interface module 106, and identification information corresponding to the network link (e.g., whether the network connection is WiFi or Ethernet). In one embodiment, the context information in the contextual data package may include all of or any subset of context information from one or more of the context categories.

The network interface module 106 receives context information, for example, by a nurse entering the information in the network interface module 106 or from a server 136. In one embodiment, by receiving this information (including, e.g., patient identification number and location), the network interface module 106 becomes exclusively assigned to the medical patient. The network interface module 106 transmits or communicates the contextual data package to clinicians during an alarm or alert, upon clinician request, or on a scheduled basis. In addition, the network interface module 106 may transmit a continuous stream of physiological information to clinicians.

By optionally connecting to multiple sensor processing modules 104 in certain embodiments, the network interface module 106 is able to associate patient context information and other context information with multiple sensor processing modules 104. Consequently, context can be created for one or more sensor processing modules 104 in addition to context being created for the network interface module 106.

In addition to transmitting the contextual data package, the network interface module 106 in one embodiment stores the contextual data package in the storage device 114. The storage device 114 may be a flash memory, a hard disk drive, or other form of non-volatile or volatile memory. In certain embodiments the storage device 114 acts as a flow control buffer. The network interface module 106 uses the storage device 114 acting as a flow control buffer to perform flow control during communications, as explained more fully below in connection with FIG. 3.

In some implementations, a server 136 may optionally be included in the physiological monitoring system 100. The server 136 in these implementations is generally a computing device such as a blade server or the like. In certain embodiments, the server 136 is an appliance server housed in a data closet. In other embodiments, the server 136 is a server located at a central nurses' station, such as a workstation server.

The server 136 receives contextual data packages from a plurality of network interface modules 106 and stores the contextual data package in a storage device 138. In certain embodiments, this storage device 138 therefore archives long-term patient data. This patient data may be maintained even after the patient is discharged. In storing patient data, the server 136 may act as an interface between the shared network and an external electronic medical record (EMR) system.

The server 136 may also store data concerning user interactions with the system and system performance metrics. Integrated into the server 136 of certain embodiments is a journal database that stores every alert and alarm or a subset of the alerts and alarms as well as human interaction in much the same way as an aviation "black box" records cockpit activity. The journal is not normally accessible to the clinical end user and, without technical authorization, cannot be tampered with. In addition, the server 136 may perform internal journaling of system performance metrics such as overall system uptime.

In one embodiment, the journaling function of the server 136 constitutes a transaction-based architecture. Certain transactions of the physiological monitoring system 100 are journaled such that a timeline of recorded events may later be re-constructed to evaluate the quality of healthcare given. These transactions include state changes relating to physiological information from the patient monitoring devices 100, to the patient monitoring devices 110, to the hospital WLAN 126 connection, to user operation, and to system behavior. Journaling related to the physiological information received from a physiological monitor in one embodiment includes recording the physiological information itself, recording changes in the physiological information, or both.

The server 136 in certain embodiments provides logic and management tools to maintain connectivity between network interface modules 106, clinician notification devices such as PDAs and pagers, and external systems such as EMRs. The server 136 of certain embodiments also provides a web based interface to allow installation (provisioning) of software rated to the physiological monitoring system 100, adding new devices to the system, assigning notifiers (e.g., PDAs, pagers, and the like) to individual clinicians for alarm notification at beginning and end of shift, escalation algorithms in cases where a primary caregiver does not respond to an alarm, interfaces to provide management reporting on the alarm occurrence and response time, location management, and internal journaling of system performance metrics such as overall system uptime (see, e.g., FIG. 5 and accompanying description).

The server 136 in certain embodiments also provides a platform for advanced rules engines and signal processing algorithms that provide early alerts in anticipation of a clinical alarm. The operating system on the server 136 in one embodiment is Linux-based for cost reasons, though a Microsoft-based or other operating system may also be used. Moreover, the server 136 is expandable to include data storage devices and system redundancy capabilities such as RAID (random array of independent disks) and High Availability options.

In another embodiment (not shown), end user devices 128, 152 include one way POCSAG Pagers having a 2 line display with audible and vibrate mode, of suitable size and durability for severe mechanical environments typical of hospital general floor settings. In yet another embodiment, the end user devices 128, 152 include two way paging systems, such as Motorola Flex and WLAN pagers. One advantage of two-way paging is the ability to confirm message receipt and the ability to remotely silence alarms. Wireless PDAs may also be used by end users based on ruggedness and acceptable form factors as determined by an end user. An example of such a device is the Symbol Technology MC50 PDA/Barcode Scanner.

Figure 2:
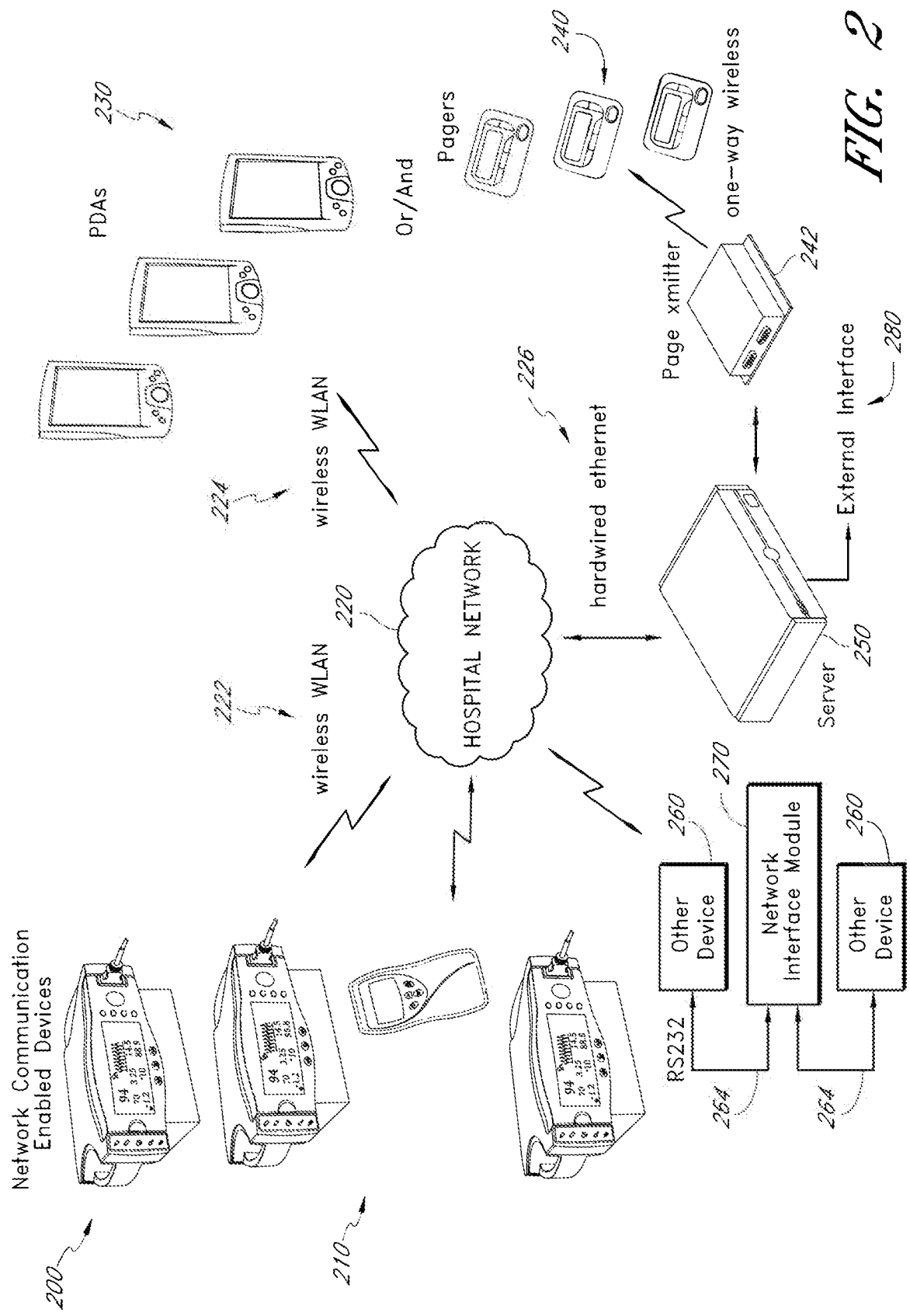
FIG. 2 is an example block diagram showing another embodiment of a physiological monitoring system.

FIG. 2 depicts another embodiment of the physiological monitoring system 200 of the present invention. The physiological monitoring system 200 includes network communications enabled devices 210. The network communications enabled devices 210 are connected directly to a hospital network 220 through a wireless connection. In certain embodiments, the network communications enabled devices 210 include sensors and sensor processing modules, similar to the sensors 102 and sensor processing modules 104 of FIG. 1. Certain of these network communications enabled devices 210 are bedside devices, and others are handheld or otherwise patient-worn devices that may be used by an ambulatory (mobile) patient.

The hospital network 220 transmits physiological information and context information to clinician notifier devices, including pagers 240, PDAs 230, and the like. In certain embodiments, the hospital network 220 utilizes a server 250 to transmit contextual data packages to a page transmitter 242, which further transmits the data to one-way wireless pagers 240. An external interface 280 may be coupled with the server 250. The external interface 280 could include one or more of the following: enterprise paging, nurse call systems, wide area paging systems, enterprise clinical and patient information systems, and third party monitoring and surveillance systems.

Certain other devices 260, such as some patient monitoring equipment, are not network communications enabled devices. That is, these other devices 260 are unable to connect to a network unaided. In the depicted physiological monitoring system 200, example devices 260 that are not network communications enabled are connected to a network interface module 270. The network interface module 270 is connected to the non-network communication enabled other devices 260 through RS232 cables 264. Such a connection is a standardized serial connection found on many devices. Because the network interface module 270 has an RS232 port, the network interface module 270 can allow non-network communication enabled patient monitoring devices to connect directly to the hospital network 220 and also to the Internet.

Moreover, by connecting to one or more other devices 260 in some embodiments, the network interface module 270 is able to associate patient context information and other context information with one or more other devices 260. Consequently, context can be created for one or more other devices 260 in addition to context being created for the network interface module 270.

Figure 3:
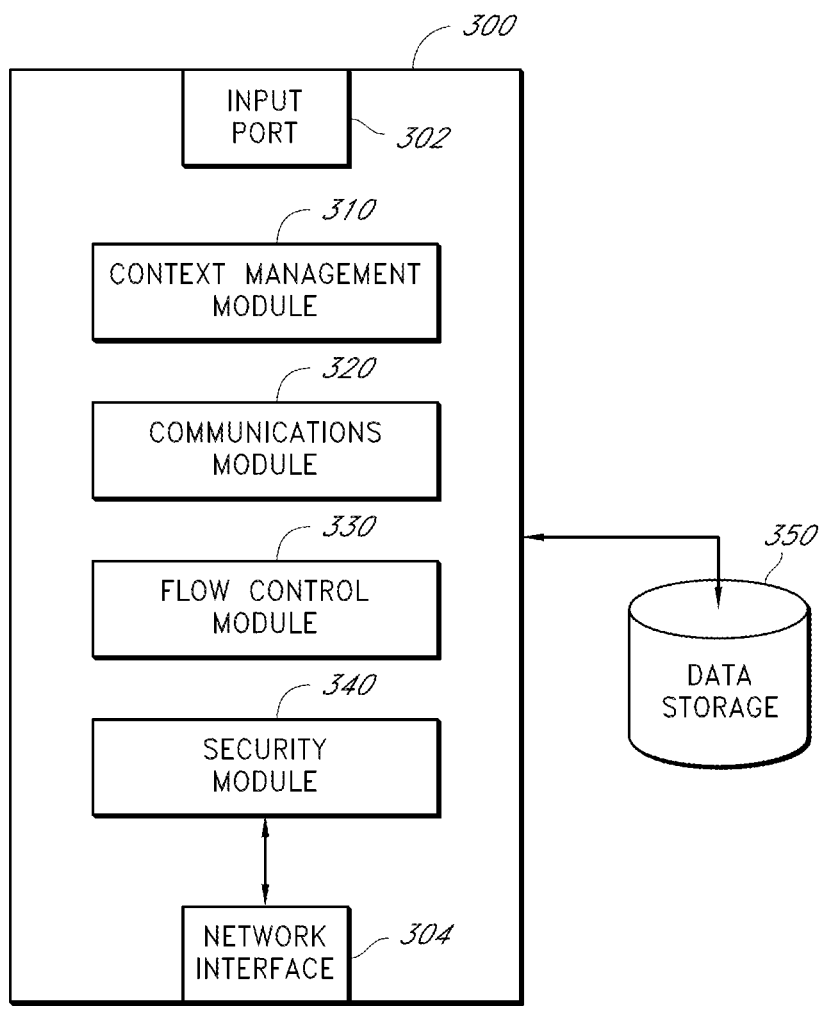
FIG. 3 is an example block diagram showing a network interface module according to some embodiments.

FIG. 3 depicts a network interface module 300 in accordance with certain embodiments of the present invention. The network interface module 300 in the depicted embodiment includes an input port 302, which in certain embodiments is a serial port for facilitating a connection to a sensor processing module. The network interface module 300 also includes a network interface 304, which may be a wired interface (e.g., Ethernet) or a wireless interface such as WiFi, Bluetooth, or the like. Alternatively, the network interface module 104 may communicate through a cable TV interface or other type of interface. Such a CTV interface provides a subcarrier bi-directional communications capability that would simultaneously co-exist with video formats.

The network interface module 300 also communicates with a storage device 350. While in the depicted embodiment the storage device 350 is shown as separate from the network interface module 300, in some implementations the storage device 350 is part of the network interface module 300. In addition, though not shown, the network interface module 300 may include a processor for implementing communications program code. Similarly, though not shown, the network interface module 300 may include an input device for a nurse to input context information and a display for receiving output from the network interface module 300.

The network interface module 300 can be integrated into handheld, portable or stationary patient monitoring platforms or instruments or contained in an accessory package with an RS 232 input for general interface to such devices. In another embodiment, (not shown) active RFID tag capabilities are included with the network interface module 106, with the clinician devices (e.g., notifier devices), or with both so that either a patient or a clinician can be located when an event occurs or on request. When operating on a shared network, the network interface module 106 is also compliant with to the open architecture communications standards of IEEE 802.1X (security and authorization), IEEE 802.3 (Ethernet), and WiFi (IEEE 802.11a, b, g, e, i wireless protocols).

A context management module 310 in the network interface module 300 manages context data. In one embodiment, the context management module 310 receives context information, such as the context information described in connection with FIG. 1 above. In one embodiment, a nurse or other clinician enters context information, such as patient name, identification number, and location, into the network interface module 300 via a keyboard or other input device (not shown) when the patient is admitted to the hospital or assigned a particular bed in the hospital. In other embodiments, the context management module 310 receives the context information from a server, such as the server 136 of FIG. 1.

The context management module 310 associates the context information with physiological information received from a sensor processing module. In certain embodiments, the context management module 310 performs this association when an alarm condition occurs. In such instances, the context management module 310 may create a contextual data package including a snapshot of historical physiological information together with the context information. In other embodiments, the context management module 310 performs an association continuously, and the network interface module 300 sends continuous or scheduled contextual data packages to end users. In addition, the context management module 310 or other modules in the network interface module 300 store the contextual data package in the storage device 350.

The communications module 320 uses the network interface 304 to communicate with a network. In certain embodiments, the communications module 320 possesses the functionality of a web server. As a web server, the communications module 320 enables the network interface module 300 to communicate with a hospital network and the Internet directly, without using a server. Consequently, other devices such as physiological monitoring devices that are not network connection enabled may connect with the network interface module and thereby become network enabled. The network interface module 300 manages the connectivity overhead for initiating and maintaining connectivity, manages context information (e.g., any of the context information described above in connection with FIG. 1), and provides a web server for displaying patient information on web-enabled devices. In one embodiment, a communications protocol based on XML technologies allows bedside devices to interface to a multitude of target end user platforms including PDAs, computer on wheels (COW), Tablet PCs, IP cell phones (smartphones), and fixed PCs.

In certain embodiments, the communications module 320 uses standard communications protocols to communicate with a network. Some examples of standard communications protocols include Ethernet, WiFi (WLAN), Bluetooth, and the like. By using standard communications protocols, the communications module 320 is able to send and receive data over a shared network or open network architecture. However, the communications module 320 may also be used on a proprietary network using proprietary protocols.

In embodiments where the network interface module 300 communicates over a shared network rather than a proprietary network, the network interface module 300 shares network resources with other devices on the network. In some cases, high-volume network traffic affects the reliability of network communications. Consequently, certain implementations of the network interface module 300 include a flow control module 330. The flow control module 330 verifies that transmitted data was received by an end user. In the event that the end user did not receive the data, the flow control module 330 resends the data stored in the storage device 350. In certain embodiments, the storage device 350 therefore acts as a flow control buffer.

A security module 340 manages user access to the network interface device 300 and to data stored in the storage device 350. In certain embodiments, the security module 340 determines whether a user attempting to connect to the network interface module 300 is authorized to do so. In one implementation, the security module 340 uses the standard IEEE.802.1X network access control protocol to manage authentication. The network interface module 106 in certain embodiments provides security and encryption to meet the Health Insurance Portability and Accountability Act (HIPAA) requirements.

In certain embodiments, the network interface module 300 incorporates all or a portion of the functionality specified by the IEEE 1073 standard and the most recent update to the IEEE 1073 standard, namely the IEEE 11703 standard, both of which are hereby incorporated by reference. In certain embodiments, the context management module 310, the communications module 320, the flow control module 330, and the security module 340 also incorporate functionality specified in the IEEE 1073 and 11703 standards. By using standard protocols, the network interface module 300 may be used to enable network communication for a wide variety of physiological monitoring devices.

Figure 4:
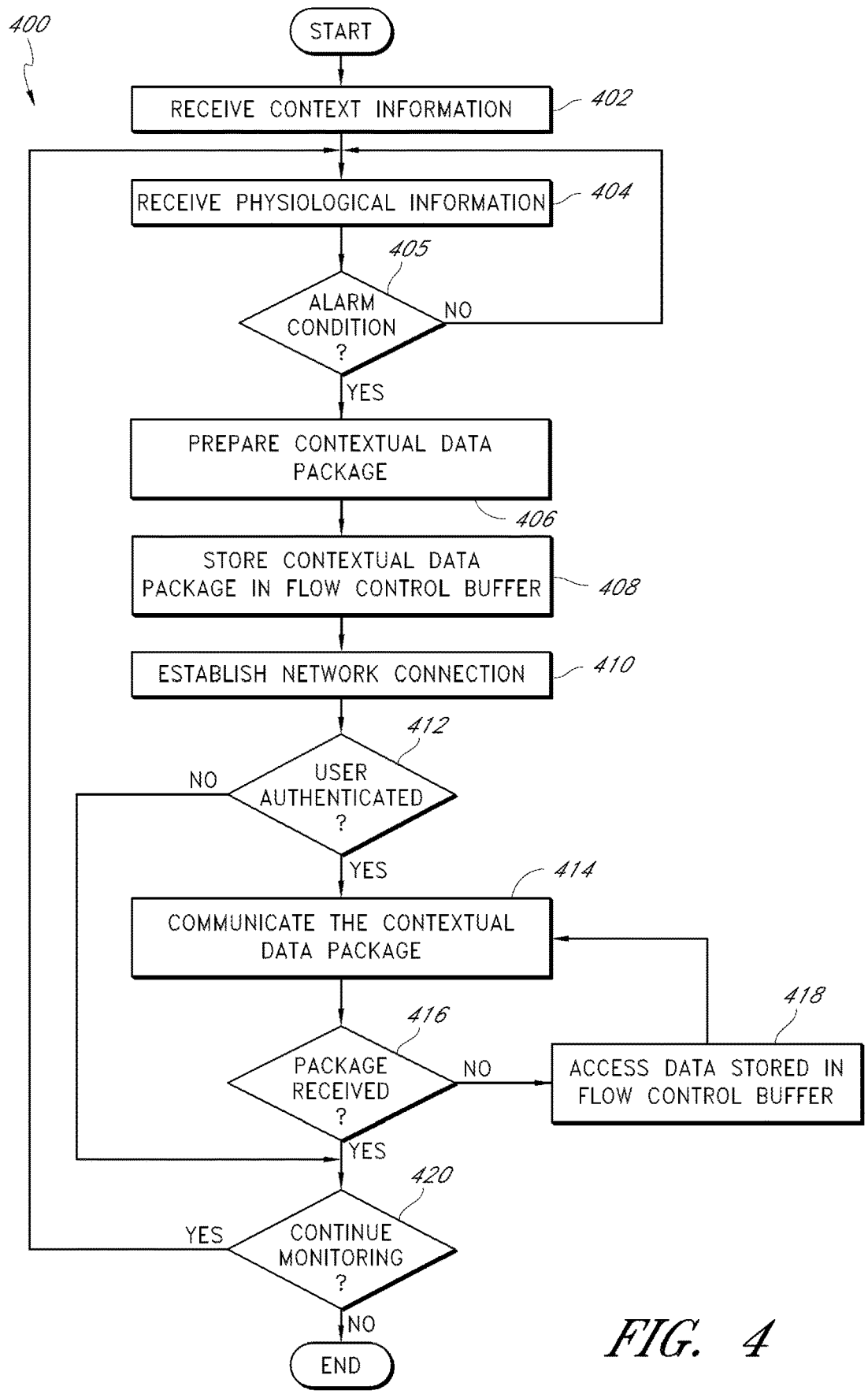
FIG. 4 is an example flowchart diagram showing a process for context-based communication of physiological information according to some embodiments.

FIG. 4 depicts a process 400 for context-based communication of physiological information according to some embodiments. In certain embodiments, the process 400 is performed by any of the network interface modules described above in connection with FIGS. 1-3. In addition, the process 400 in certain embodiments may be performed by any of the physiological monitoring systems described in connection with FIGS. 1, 2, and 5.

The process 400 begins by receiving context information at 402. In one embodiment, a device such as a network interface module receives the context information once, such as in an initialization step. The process 400 then receives physiological information at 404. In certain embodiments, the process 400 continues to receive physiological information throughout the remaining steps of the process 400. Alternatively, the process 400 may receive physiological information 400 for a portion of the process 400.

At 405, the process 400 determines whether an alarm condition or alert has occurred. If an alarm condition or alert has occurred, the process 400 proceeds to 406. However, if an alarm condition or alert has not occurred, the process 400 loops back to 404. In one embodiment, the looping back of the process 400 to 404 represents that a network interface module continually receives physiological information until an alarm condition or alert occurs. In certain embodiments (not shown), the process 400 may continue to receive physiological information even when an alarm condition or alert occurs.

At 406 the process 400 prepares a contextual data package. The contextual data package may include context information and a snapshot of physiological information. In one embodiment, the snapshot of physiological information includes the physiological information that gave rise to an alarm or alert. In one embodiment, the snapshot of physiological information includes information both before and after the occurrence of an alarm or alert. The contextual data package is stored in a flow control buffer at 408.

At 410, the process 400 establishes a network connection. In one embodiment, establishing a network connection at 410 includes connecting a network interface module to an end user device, such as a notifier device assigned to a nurse during his or her work shift. The process 400 then determines at 412 whether the user of the device (e.g., the nurse) has been authenticated. If the user has not been authenticated, the process 400 proceeds to 420. On the other hand, if the user has been authenticated, the process 400 proceeds to 414.

The process 400 at 414 communicates the contextual data package to the user. At 416, the process 400 determines whether the contextual data package was received. If the contextual data package was received, the process 400 proceeds to 420. Otherwise, the process 400 proceeds to 418, where the process 400 accesses data stored in the flow control buffer. In one embodiment, the data accessed by the process 400 is equivalent to or substantially equivalent to the contextual data package communicated to the user at 414.

The process 400 then loops back to 414, where the process 400 communicates (e.g., resends) the contextual data package to the user, and then at 416 re-verifies that the package was received. The process 400 in some implementations continues to loop between steps 414, 416, and 418 until the contextual data package was received. Thus, steps 414, 416, and 418 in certain embodiments constitute flow control performed by the process 400. These flow control steps allow the process 400 to overcome network transmission errors which may occur in shared networks.

If the contextual data package was received, the process 400 evaluates whether to continue the monitoring of physiological information at 420. If the process 400 determines to continue monitoring, the process loops back to 404, where the process 400 continues to receive physiological information. If, however, the process 400 determines not to continue monitoring, the process 400 ends.

In various embodiments of the process 400, the contextual data package or the physiological information alone is transmitted to the user even in the absence of an alarm condition. In still other embodiments, fewer than all of the steps are performed, or the steps are performed in different order. For instance, the process 400 may only perform the steps of receiving physiological information at 404, preparing a contextual data package at 406, establishing a network connection at 410, and communicating the contextual data package to the user at 414.

Figure 5:
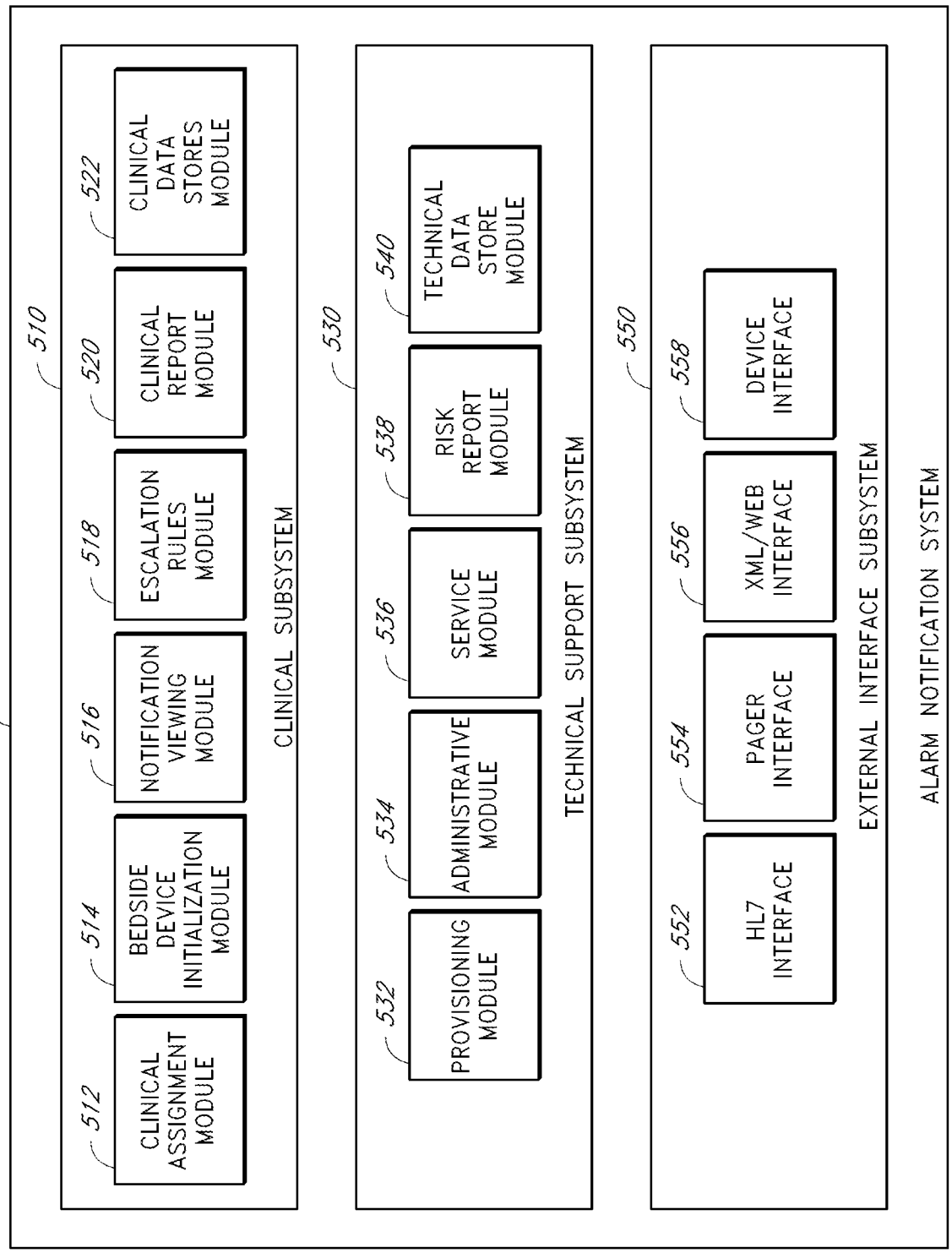
FIG. 5 is an example block diagram showing an alarm notification system according to some embodiments.

FIG. 5 depicts an alarm notification system 500 in accordance with certain embodiments of the present invention. A clinical subsystem 510 defines the major software components of alarm notification system 500 including a clinical assignment module 512, a bedside device initialization module 514, a notification and viewing module 516, an escalation rules module 518, a clinical report module 520, and a clinical data stores module 522. An authentication feature is built into mobile computing devices in compliance with HIPAA and hospital IT policies.

The clinical assignment module 512 has an assignment function. A nursing supervisor assigns individual nurses to specific patients at the start of each shift and upon admission of new patients. Shift assignments take place at change of shift during a "report" transition exercise where individual nurses and nursing supervisor from previous shift "hand off" patients to the next shift. The report can be either formal where all nurses attend or informal dependent on hospital nursing service policies and procedures. The clinical assignment module 512 provides an intuitive interface that allows a listing of available nurses to be assigned individual patients. The major user of this module is the unit clerk as assigned by the nursing supervisor. A nurse can be assigned one or more patients or all patients. An alternative work flow is self assignment where individual nurses assign patients themselves in which case they perform functions of the unit clerk. In the self assignment model, a default is implemented where any unassigned patient is either assigned to all nurses or the nursing supervisor.

The bedside device initialization module 514 has bedside devices, such as the network interface modules described above, that are sometimes set up by an aide to the nurse. In the case where the nurse performs this task, she or he performs the functions of the nursing aide. Work flow includes delivering a device to bedside, applying sensors, initializing the device, and setting patient context, such as name, ID and location.

The notification and viewing module 516 assigns a wireless notification device, such as a one-way pager, PDA, IP telephone, COW, or Tablet to individual nurses. The device becomes associated with her or him. Alarms are routed to the notification device based on the clinical assignment module 512. Non-dedicated notifier solutions such as hospital owned paging systems issued to nurses have unknown latency characteristics. A general purpose interface is available at the server with a latency of less than 1 second upon receipt from the bedside device and is time stamped upon presentation to the server external interface and stored in a journaling system within the server. An additional interface for mobile computing platforms such as PDA, COWS, and Tablets allows viewing of current and trend data for an individual patient.

The escalation rules module 518 has a rules engine that actuates an escalation policy defined by the hospital. The escalation rules module 518 provides alternative routing of alarms to alternative and additional clinical users in the event an alarm is not responded to or persists for a predefined (e.g., by a policy) period of time. The escalation rules module 518 in certain embodiments routes alarms to an emergency response team.

The clinical report module 520 provides predefined formatted reports on the clinical data from which to determine physiologic condition and/or progress. More than one report may be dependent on end user needs. Reports are not time critical views of individual patients and may be remotely viewed by clinicians who have alarm notification system 500 privileges and have been authenticated by the alarm notification system 500. These reports are web browser views that allow clinicians to set viewing parameters such as time and parameter scales and alarm review.

The clinical data stores module 522 provides data storage and database resources to store information as known to those skilled in the art.

Further shown in FIG. 5, a technical support subsystem 530 is isolated from the clinical subsystem 510 in compliance with HIPAA and as such does not allow viewing or access to any patient information with the exception of the risk report module 538. The technical support subsystem 530 includes a provisioning module 532, an administration module, a service module 536, a risk report module 538, and a technical data store module 540.

The provisioning module 532 provides provisioning, which is the initial installation of the system and first customer use. The primary user of the provisioning module 532 is the field installer. The provisioning module 532 contains all the start up scripts and system configurations to bring the system from shipping boxes to full alarm notification system 500 functionality. Provisioning includes steps to configure individual devices, notifiers such as pagers, PDA, COW, Tables and IP telephone at the customer site, preferably by wireless means (e.g., Bluetooth).

The administrative module 534 provides a system interface for the application administrator to set up users, set policies for various actor privileges such as a nurses aide being able to set or change alarms, set up allowed device connection identifications, and other general systems administrative duties typical of IT systems.

The service module 536 provides interfaces for various technical support actors including remote service, IT Service, and Biomed Service. Each of these actors may perform each others' functions. Interfaces allow the service actors to access system performance data to access performance, for example, data traffic, device assets connected, software version management, CPU loading, network loading, etc. and execute remote technical service procedures, for example, resetting a printer queue, repartition of disk, uploading software patches, etc. The service module 536 includes a full journaling function that stores every user interaction or a portion of user actions that can be captured by the system, especially changes in default values or alarm settings.

The risk report module 538 provides summary reports on alarm occurrences, duration of alarm, clinical response time to alarms and other statistical data to determine overall effectiveness of clinical response to alarms in compliance with JCAHO, other regulatory bodies, and internal quality assurance committees.

The technical data stores module 540 has the same characteristics as the clinical data stores module 522 except that the technical data stores module 540 is used for technical data. The technical data stores module 540 may or may not share the same physical and logical entity as the clinical data stores module 522.

Additionally shown in FIG. 5, an external interface subsystem 550 provides interfaces to bedside devices and external systems such as electronic medical records, admit discharge, transfer systems, POCSAG pager systems, middleware engines such as Emergin, and Web/XML enabled devices such as wireless PDAs, COWs and Tablet PCs. The external interface subsystem 550 has an HL7 interface 552, a pager interface 554, an XML/Web interface 556, and a device interface 558.

The HL7 interface 552 provides a bi-directional interface to electronic medical records (EMR) and supports both push and pull models. The push model is when a bedside nurse initiates data transfer. The pull model is when an EMR system polls the alarm notification system 500 server. The pager interface 554 provides output to external paging system. Message latency is identified to an end user for any user-owned paging solution. This same output can be used for middleware alarm notification systems such as Emergin. The XML/Web interface 556 provides bi-directional interface with mobile computing platforms such as wireless PDA, COWs, Tables, and Web-enabled IP phones. Mobile computing platforms support Web Browser XML applications. The device interface 558 provides a bi-directional interface to bedside devices as well as to other devices enabled by the communications module or accessory. Application Programmer Interface (API) capability is an option for interfacing to other bedside devices.

The major end users of the alarm notification system 500 system (not shown or described for simplicity) include hospital electronic medical records, admit discharge transfer, pharmacy, clinical information, patient flow tracking and others. Actors, e.g., users of the alarm notification system 500, including clinical actors and technical support actors. The clinical actors include nursing supervisors, unit clerks, nursing aides, nurses, rapid response teams and respiratory therapists.

A nursing supervisor assigns individual nurses to specific patients at the beginning of each shift. Shift can vary according to hospital staffing policies. A unit clerk takes direction from the nursing supervisor, typically inputs assignments into system and monitors overall system. A unit clerk may not be available for all shifts. A nursing aide takes assignments from nurse or nursing supervisor, typically applies bedside device sensor, initializes the bedside device and sets alarms to default values. A nurse has primary responsibility for individual patient care and primary response to alarms. The nurse is assigned by nursing supervisor to more than one patient dependent on her/his skills and patient needs and is not always assigned the same patient. Nursing aides are not found in all hospitals.

A rapid response team responds to clinical emergencies initiated by either a bedside nurse or a nursing supervisor. The team supports more than one care unit and has one or more members depending on shift. Rapid Response Teams may not be implemented in all hospitals. A respiratory therapist has responsibilities for management of respiratory care for more than one patient and usually more than one care unit. Respiratory therapists are not found in some international settings.

Clinical actor performance substitution allows a high capability actor to assume the roles of other actors. Alarm notification system 500 allows mechanisms for such performance. For example, a nursing supervisor may perform functions of a unit clerk nursing aide, a nurse and a rapid response team. A nurse may perform functions of a unit clerk, a nursing aide and a rapid response team. In some international markets a nurse may perform the functions of a respiratory therapist.

The technical support actors include field installers, application administrators, remote services, IT engineers, biomedical engineers and risk managers. A field installer provisions the system for initial installation, installs components, and validates that the installation and configuration meet a purchasing contract. An application administrator sets up and maintains user accounts and systems defaults. A remote service provides remote diagnostics and system maintenance over a remote link, such as dial up and VPN. An IT engineer provides network support services if the system is integrated with the hospital IT network. A biomedical engineer provides bedside and system primary service. A risk manager reviews reports for quality and risk mitigation purposes. Technical support actors may also fill in for other actors. For example, an IT engineer, a biomedical engineer, or a remote service can perform the functions of an application administrator. An IT engineer or a biomedical engineer can perform each other's functions.

In certain embodiments, systems and methods are provided for rapidly storing and acquiring physiological trend data. For instance, physiological information obtained from a medical patient can be stored in a round-robin database. The round-robin database can store the physiological information in a series of records equally spaced in time. Parameter descriptors may be used to identify parameter values in the records. The parameter values can be dynamically updated by changing the parameter descriptors to provide for a flexible database. In addition, the size of files used in the database can be dynamically adjusted to account for patient condition.

Additionally, in certain embodiments, medical data obtained from a clinical network of physiological monitors can be stored or journaled in a journal database. The medical data can include device events that occurred in response to clinician interactions with one or more medical devices. The medical event data may also include device-initiated events, such as alarms and the like. The medical data stored in the journal database can be analyzed to derive statistics or metrics, which may be used to improve clinician and/or hospital performance.

As used herein the terms "round-robin database" and "RRDB," in addition to having their ordinary meaning, can also describe improved database structures having unique characteristics and features disclosed herein. Sometimes these structures are referred to herein as dynamic RRDBs or adaptive RRDBs.

Figure 6:
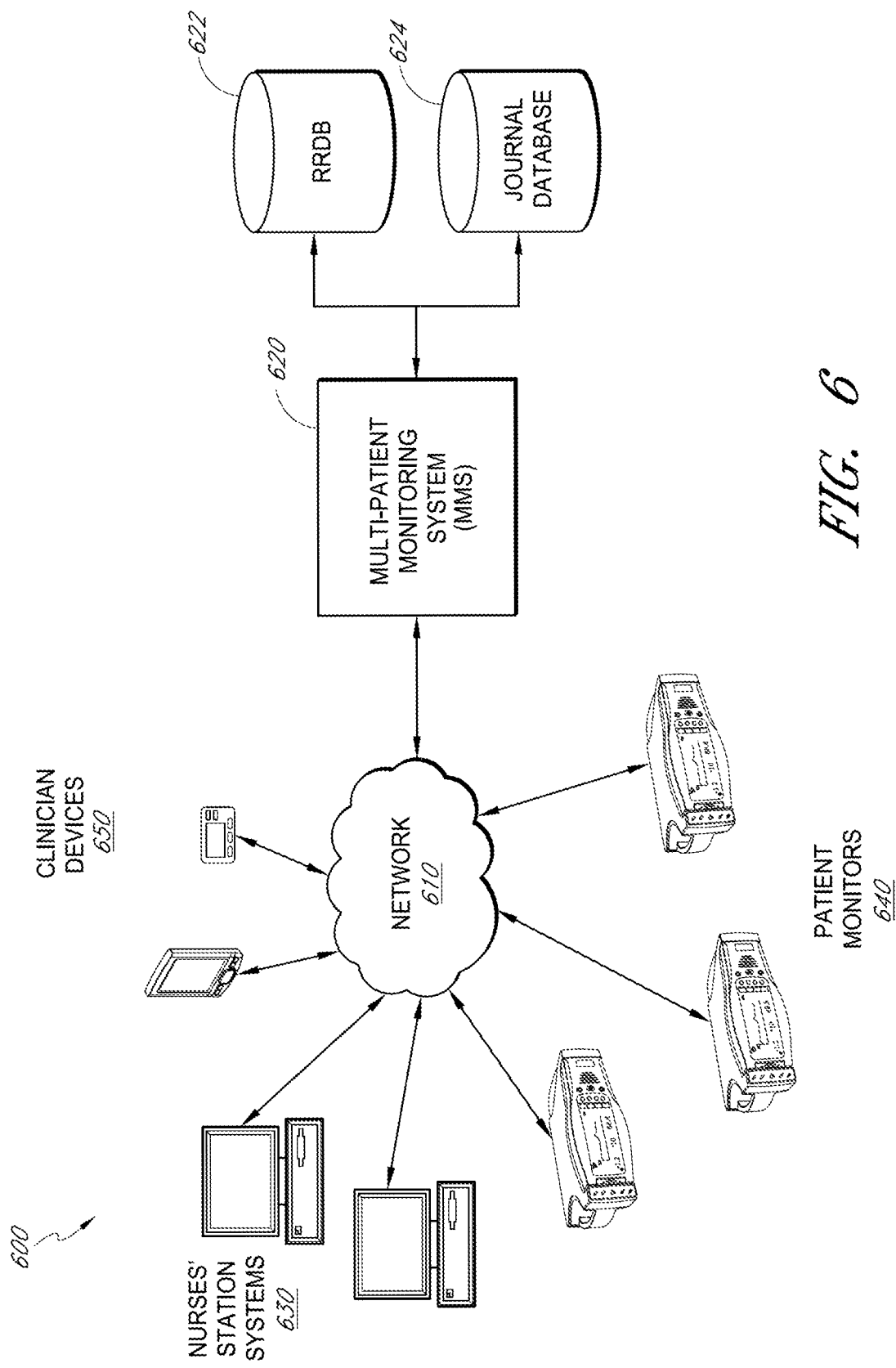
FIG. 6 is a block diagram illustrating an embodiment of a clinical network environment.

FIG. 6 illustrates an embodiment of a clinical network environment 600. The clinical network environment 600 includes a multi-patient monitoring system (MMS) 620 in communication with one or more patient monitors 640, nurses' station systems 630, and clinician devices 650 over a network 610. In certain embodiments, the MMS 620 provides physiological data obtained from the patient monitors 640 to the nurses' station systems 630 and/or the clinician devices 650. Additionally, in certain embodiments, the MMS 620 stores physiological information and medical event information for later analysis.

The network 610 of the clinical network environment 600 can be a LAN or WAN, wireless LAN ("WLAN"), or other type of network used in any hospital, nursing home, patient care center, or other clinical location. For ease of illustration, the remainder of this specification will describe clinical environments in the context of hospitals; however, it should be understood that the features described herein may also be employed in other clinical locations or settings. In some implementations, the network 610 can interconnect devices from multiple hospitals or clinical locations, which may be remote from one another, through the Internet, a leased line, or the like. Likewise, the various devices 620, 630, 640, and 650 of the clinical network environment 100 may be geographically distributed (e.g., among multiple hospitals) or co-located (e.g., in a single hospital).

The patient monitors 640 may be point-of-care (POC) instruments or the like that monitor physiological signals detected by sensors coupled with medical patients. The patient monitors 640 may process the signals to determine any of a variety of physiological parameters. One example of a physiological parameter is blood oxygen saturation ($SpO_2$). Other examples of physiological parameters are described below with respect to FIG. 7.

The patient monitors 640 can provide the physiological information to the MMS 620. The patient monitors 640 can also provide information on medical events, such as alarms, to the MMS 620. Alarms can be triggered, for example, in response to a physiological parameter falling outside of a normal range. Alarms can also include alerts regarding equipment failures, such as a probe-off condition where a sensor has fallen off of a patient. Other examples of medical events are described below with respect to FIG. 7.

In various embodiments, the patient monitors 640 provide the physiological information and medical events to the MMS 620. The MMS 620 is described in greater detail below. In some implementations, the patient monitors 640 may provide at least some of this information directly to the nurses' station systems 630 and clinician devices 650.

The nurses' station systems 630 can be desktop computers, laptops, work stations, or the like that are located at a nurses' station. One or more nurses' station computers 630 can be located at a single nurses' station. The nurses' station computers 630 can receive and display physiological information and alarm data received from the MMS 620 (or monitors 640). In certain embodiments, the nurses' station computers 630 use a graphical user interface (GUI) that provides a streamlined, at-a-glance view of physiological and medical information. An example of this GUI is described below with respect to FIG. 9.

The clinician devices 650 can include any of a variety of devices used by clinicians, such as pagers, cell phones, smart phones, personal digital assistants (PDA), laptops, tablet PCs, personal computers, and the like. The clinician devices 650 are able to receive, in some embodiments, physiological information and alarms from the MMS 620 (or monitors 640). Physiological and alarm data can be provided to a particular clinician device 650, for example, in response to an alarm. The clinician devices 650 can, in some instances, receive values and waveforms of physiological parameters.

The MMS 620 in certain embodiments includes one or more physical computing devices, such as servers, having hardware and/or software for managing network traffic in the network 610. This hardware and/or software may be logically and/or physically divided into different servers 620 for different functions, such as communications servers, web servers, database servers, application servers, file servers, proxy servers, and the like.

The MMS 620 can use standardized protocols (such as TCP/IP) or proprietary protocols to communicate with the patient monitors 640, the nurses' station computers 630, and the clinician devices 650. In one embodiment, when a patient monitor 640 wishes to connect to the MMS 620, the MMS 620 can authenticate the patient monitor 640 and provide the monitor 640 with context information of a patient coupled to the monitor 640. Context information can include patient demography, patient alarm settings, and clinician assignments to the patient, among other things. Examples of context information are described herein. The MMS 620 may obtain this context information from the nurses' station systems 630 or other hospital computer systems, where patient admitting information is provided.

Upon connecting to a patient monitor 640, the MMS 620 may receive physiological information and medical events from the patient monitors 640. The MMS 620 may provide at least a portion of the physiological information and events to the nurses' station systems 630 and/or clinician devices 650. For example, the MMS 620 may provide physiological data and alarms for a plurality of patient monitors 640 to a nurses' station system 630, where nurses can evaluate the data and/or alarms to determine how to treat patients. Similarly, the MMS 620 may send wireless pages, emails, instant messages, or the like to clinician devices 650 to provide clinicians with physiological data and alarms.

Advantageously, in certain embodiments, the MMS 620 can store physiological information obtained from the patient monitors 640 in a round-robin database (RRDB) 624. The RRDB 622 of various embodiments includes a streamlined database structure that facilitates rapidly storing and retrieving patient data. The RRDB 622 can therefore be used in certain embodiments to rapidly provide physiological trend data to the nurses' stations 630 and to the clinician devices 650. Thus, for example, if a clinician desires to see a patient's physiological trends over a certain time period, such as the past hour, the clinician can use a nurses' station computer 630 or clinical device 650 to query the MMS 620. The MMS 620 may then obtain physiological information corresponding to the desired time period from the RRDB 622. Advantageously, the RRDB 622 can enable faster acquisition of trend data then is possible with relational databases currently used by hospital monitoring systems. Additional uses and optimizations of the RRDB 622 are described below.

In certain embodiments, the MMS 620 also archives or stores information about medical events in a journal database 624. The medical events can include events recorded by devices such as the patient monitors 640, nurses' station systems 630, and clinician devices 650. In particular, the medical events can include device events that occur in response to a clinician's interaction with a device, such as a clinician-initiated deactivation of an alarm. The medical events can also include device events that occur without a clinician's interaction with the device, such as the alarm itself. Additional examples of medical events are described below with respect to FIG. 7.

The MMS 620 may analyze the medical event information stored in the journal database 624 to derive statistics about the medical events. For example, the MMS 620 can analyze alarm events and alarm deactivation events to determine clinician response times to alarms. Using these statistics, the MMS 620 may generate reports about clinician and and/or hospital performance. Advantageously, in certain embodiments, these statistics and reports may be used to improve the performance of clinicians and hospitals.

For instance, in certain situations, the reports might help hospitals discover the cause of issues with patient monitors 640. The following example scenario can illustrate potential benefits of such a report. $SpO_2$ alarm levels tend to be different for adults and neonates. However, some clinicians may not know this and may modify neonate $SpO_2$ monitors to include adult alarm levels. These changes can result in many false alarms, which may cause clinicians to become frustrated and avoid using the patient monitors 640. By journaling medical events such as clinician alarm changes, it can be determined by an analysis of the journaled data that clinicians were inappropriately adjusting alarm settings on neonate monitors. A hospital could then use this information to take corrective action, such as by fixing the alarm limits and training the clinicians.

Although not shown, administrative devices may be provided in the clinical network environment 600. The administrative devices can include computing devices operated by hospital administrators, IT staff, or the like. Using the administrative devices, IT staff may, for example, promulgate changes to a plurality of patient monitors 640, nurses' station systems 630, and the MMS 620. The administrative devices may also allow IT staff to interface third-party systems with the MMS 620, such as electronic medical record (EMR) systems. The third party systems may be used, for instance, to change alarm settings on a plurality of monitors from an administrative device. Actions performed by administrators, IT staff, and administrative devices in general may also be journaled in the journal database 624.

Figure 7:
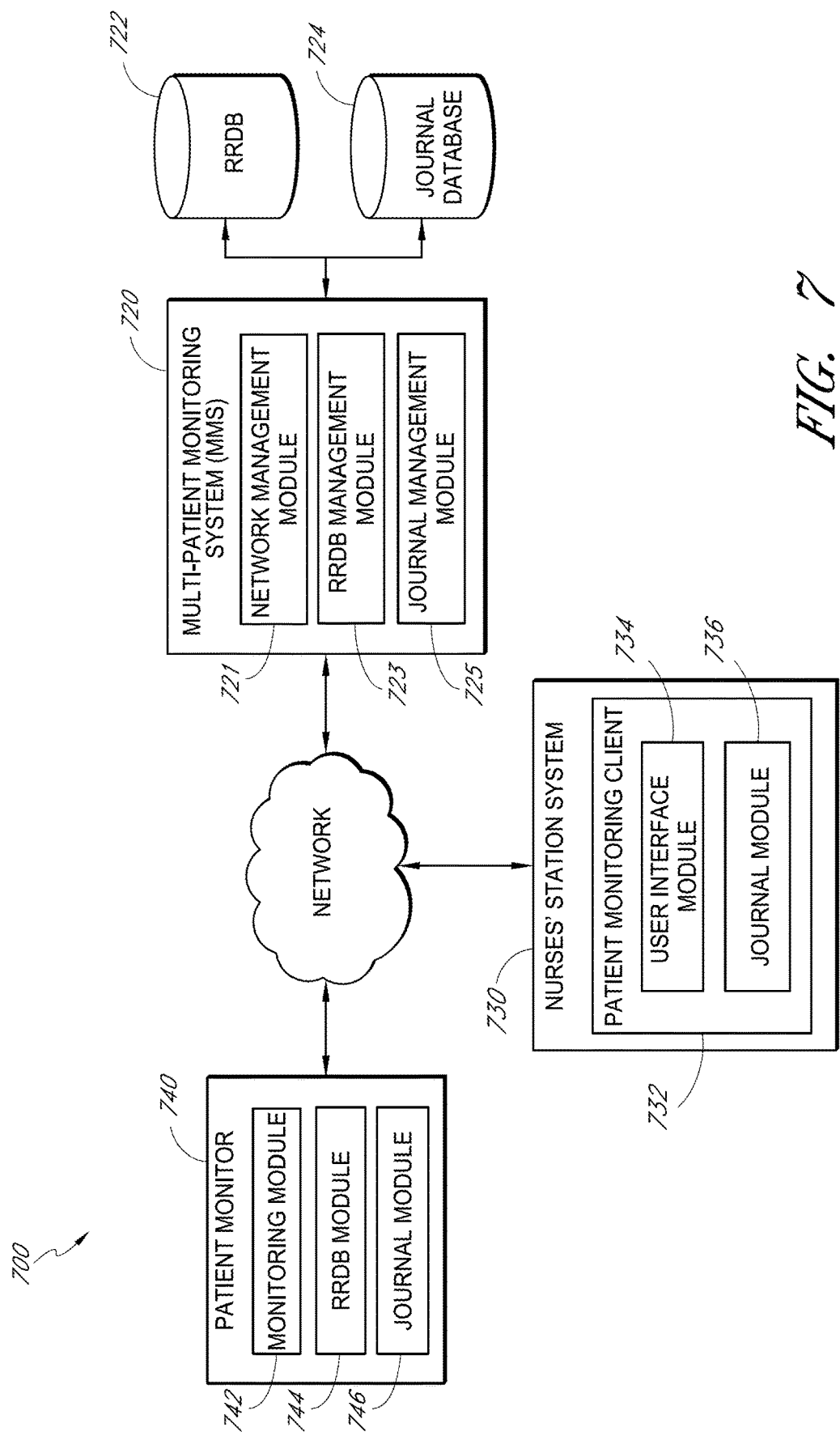
FIG. 7 is a block diagram illustrating a more detailed embodiment of the clinical network environment of FIG. 6.

FIG. 7 illustrates a more detailed embodiment of a clinical network environment 700. The clinical network environment 700 includes a network 710, a patient monitor 740, a nurses' station system 730, an MMS 720, an RRDB 722, and a journal database 724. These components may include all the functionality described above with respect to FIG. 6.

One monitor 740 and nurses' station system 730 are shown for ease of illustration. In addition, although not shown, the clinician devices 750 described above may also be included in the clinical network environment 700.

The depicted embodiment of the patient monitor 740 includes a monitoring module 742, an RRDB module 744, and a journal module 746. Each of these modules may include hardware and/or software. Other components, such as a communications module, are not shown but may be included in the patient monitor 740 in various implementations.

The monitoring module 742 can monitor physiological signals generated by one or more sensors coupled with a patient. The monitoring module 742 may process the signals to determine any of a variety of physiological parameters. For example, the monitoring module 742 can determine physiological parameters such as pulse rate, plethysmograph waveform data, perfusion index, and values of blood constituents in body tissue, including for example, arterial carbon monoxide saturation ("HbCO"), methemoglobin saturation ("HbMet"), total hemoglobin ("HbT" or "SpHb"), arterial oxygen saturation ("$SpO_2$"), fractional arterial oxygen saturation ("$SpaO_2$"), oxygen content ("$CaO_2$"), or the like.

In addition, the monitoring module 742 may obtain physiological information from acoustic sensors in order to determine respiratory rate, inspiratory time, expiratory time, inspiration-to-expiration ratio, inspiratory flow, expiratory flow, tidal volume, minute volume, apnea duration, breath sounds, rales, rhonchi, stridor, and changes in breath sounds such as decreased volume or change in airflow. In addition, in some cases the monitoring module 742 monitors other physiological sounds, such as heart rate (e.g., to help with probe-off detection), heart sounds (e.g., S1, S2, S3, S4, and murmurs), and changes in heart sounds such as normal to murmur or split heart sounds indicating fluid overload. Moreover, the monitoring module 742 may monitor a patient's electrical heart activity via electrocardiography (ECG) and numerous other physiological parameters.

In some implementations, the patient monitors 740 may also determine various measures of data confidence, such as the data confidence indicators described in U.S. Pat. No. 7,024,233 entitled "Pulse oximetry data confidence indicator," the disclosure of which is hereby incorporated by reference in its entirety. The patient monitors 740 may also determine a perfusion index, such as the perfusion index described in U.S. Pat. No. 7,292,883 entitled "Physiological assessment system," the disclosure of which is hereby incorporated by reference in its entirety. Moreover, the patient monitors 740 may determine a plethysmograph variability index (PVI), such as the PVI described in U.S. Publication No. 2008/0188760 entitled "Plethysmograph variability processor," the disclosure of which is hereby incorporated by reference in its entirety. The parameters described herein are merely examples, and many other parameters may be used in certain embodiments.

In certain embodiments, the RRDB module 744 receives physiological information from the monitoring module 742 and transmits the physiological information over the network 710 to the MMS 720. In response, the MMS 220 may store the physiological information in the RRDB 722. Advantageously, in certain embodiments, the RRDB module 744 associates the physiological information with parameter descriptors prior to transmittal to the MMS 720. The parameter descriptors may be identifiers that the RRDB module 744 associates with each measured physiological parameter value. The MMS 720 may use these parameter descriptors to identify the types of measured parameters received from the RRDB module 744.

The parameter descriptors may be descriptors generated according to a markup language specification, such as an extensible markup language (XML) specification. As such, the parameter descriptors may include tags that enclose measured physiological values. These tags may be machine readable or human readable. For instance, the tags may include numerical identifiers (e.g., "0017") or descriptive identifiers, such as "SPO2" or "SPHB." A simplified example stream of physiological information from an SpO$_2$ sensor and an SpHb sensor associated with parameter descriptors might be as follows: <SPO2>96</SPO2> <SPHB>14.1</SPHB> <SPO2>97</SPO2> <SPHB>14.0</SPHB>, and so on.

In one embodiment, the RRDB module 744 may have stored (e.g., in a data file) a set of predefined parameter descriptors available for the patient monitor 740. These parameter descriptors may correspond to possible parameters that may be measured by the patient monitor 740. The parameter descriptors transmitted by the RRDB module 744 may depend on the particular subset of parameters measured by the patient monitor 740.

If an additional (or different) parameter is subsequently measured by the patient monitor 740, the RRDB module 740 may dynamically update the parameter descriptors that are sent to the MMS 720. Likewise, if the patient monitor 740 ceases to measure one of the parameters, the RRDB module 744 may cease to transmit the corresponding parameter descriptor to the MMS 720.

The patient monitor 740 also includes a journal module 746 in the depicted embodiment. The journal module 740 may record medical events related to the patient monitor 740. These medical events can include clinician-initiated events, such as changes to alarm settings (e.g., maximum and minimum permitted parameter values), types of parameters monitored/sensors connected to the patient monitor 740, and the like. The journal module 746 may record these events by, for example, acting as a key logger or the like to record button presses of a clinician. The journal module 746 may also include current-sense circuitry to detect when sensors or cables are connected to the monitor 740, and so forth. The medical events may also include non-clinician initiated events, such as alarms and alerts. The medical events can also include events from administrative devices (not shown), such as EMR updates to alarm settings across the network 710.

The journal module 746 may log these events locally at the patient monitor 740. In addition, or instead of logging the events locally, the journal module 746 may transmit information about the events to the MMS 720. In turn, the MMS 720 can store the event information in the journal database 724.

The nurses' station system 730 is shown in the depicted embodiment having a patient monitoring client 732. The patient monitoring client 732 can enable the nurses' station system 730 to receive and display physiological information and alarm information. The patient monitoring client 732 includes a user interface module 734. The user interface module 734 may include, for example, software for displaying physiological information, patient information, and medical event information for a plurality of patient monitors 740. The user interface module 734 may also allow clinicians to admit and discharge patients, remotely modify device alarm limits, and the like. An example user interface that may be generated by the user interface module 734 is described below with respect to FIG. 9.

The patient monitoring client 732 further includes a journal module 736. The journal module 736 may include software for recording medical events related to the patient monitoring client 732. For example, the journal module 736 may record which clinicians login to and logoff of the patient monitoring client 732 and when these events occur; admit and discharge events; and other clinician keystrokes, mouse clicks, and interactions with the patient monitoring client 732. The journal module 736 may log this event information locally at the nurse's station system 730 and/or transmit the event information to the MMS 720.

As shown, the MMS 720 may include a network management module 721, an RRDB management module 723, and a journal management module 725, each of which may include one or more software components. In one embodiment, the network management module 721 receives messages containing physiological information and medical event data from the patient monitor 740. The network management module 721 can provide at least a portion of this data to the nurses' station system 730 and clinician devices 650 of FIG. 6. The network management module 721 can also provide the physiological information to the RRDB management module 723 and provide the medical event data to the journal management module 725.

In certain embodiments, the RRDB management module 723 stores the physiological information received from the patient monitor 740 in the RRDB 722. When the patient monitor 740 initially connects to the MMS 720, or at another time, the RRDB management module 723 can create one or more RRDB files in the RRDB 722 corresponding to the patient monitor 740. The contents of this file or files may depend on the type of patient monitor 740, which may be defined by the patient monitor's 740 serial number, model number, vendor identifier, combinations of the same, or the like. Specific examples of the structure and contents of RRDB files are described in US Patent Publication 2009/0119330, the entire contents of which are hereby incorporated by reference herein.

The RRDB management module 723 can also provide physiological trend data stored in the RRDB to the network management module 721 for transmittal to monitors 740, nurses' station systems 730, and/or clinician devices. The RRDB management module 723 may also provide physiological data from the RRDB 722 to the journal management module 725 for purposes described below with respect to FIG. 8B.

The journal management module 725, in certain implementations, receives medical event data from the monitor 740 and the nurses' station system 730 and stores this data in the journal database 724. In an embodiment, the journal database 724 is a relational database; however, other structures may be used. Each entry of event data may have a corresponding time stamp that indicates when an event occurred. This time stamp may be provided by the journal modules 746 or 736 or by the journal management module 725. The journal management module 725 may also store event counters in the journal database 724 that reflect a number of times medical events occurred. For example, counters could be stored that count how many alarms occurred within a period of time or how many times a clinician logged on or logged off of a network device.

Advantageously, the journal management module 725 may, in certain embodiments, analyze the medical data in the journal database 724 to determine statistics or metrics of clinician and/or hospital performance. The journal management module 725 may provide an interface to users of the nurses' station system 730 or another computing device to access these statistics. In one example embodiment, journal management module 725 can analyze alarm events and alarm deactivation events to determine clinician response times to alarms. The journal management module 725 may further determine the clinician response times in nurses' day and night shifts. The journal management module 725 may generate reports of these statistics so that hospital administrators, for example, may determine which shifts perform better than others.

More generally, the journal management module 725 may generate reports about clinician and and/or hospital performance by analyzing various statistics derived from data in the journal database 724. One example of a report is a monitoring report card, which grades a given hospital against other hospitals (or nurses' station against nurses' station, and the like) based at least partly on the derived statistics. Advantageously, hospital administrators, clinicians, and the like may use these statistics and reports to improve the clinician and hospital performance.

Some or all of the features of the clinical network environment 700 may be adapted in certain embodiments. For instance, either or both of the journal modules 746 or 736 may perform some or all of the functions of the journal management module 725. Likewise, one or more journal databases 724 may be stored at the patient monitor 740 and/or nurses' work station 730. Similarly, the RRDB module 724 may perform some or all of the functions of the RRDB management module 723, and an RRDB 722 may be stored at the patient monitor 740. In addition, in some implementations, the clinician devices 650 of FIG. 6 may have RRDB and/or journal modules as well. Many other adaptations, configurations, and combinations may be made in other embodiments. Additional information regarding embodiments of the RRDM can be found in US Patent Publication 2009/0119330.

Figure 8A:
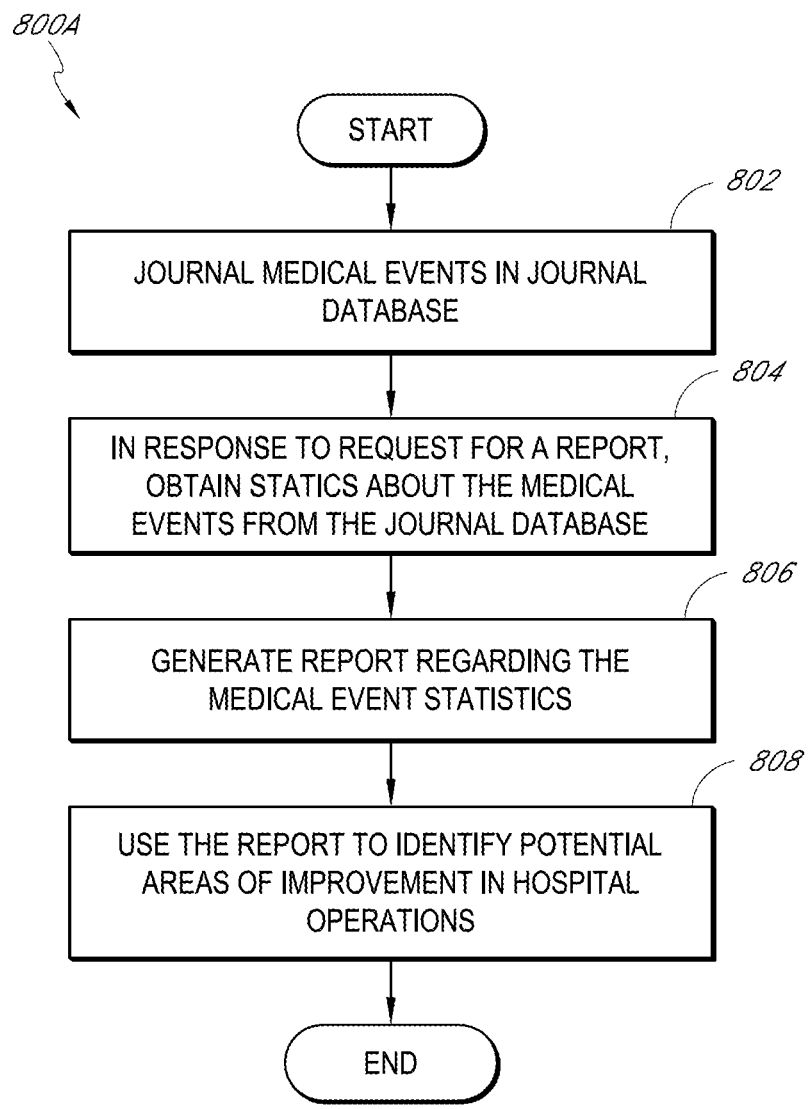
FIG. 8A is a flow chart illustrating an embodiment of a process for journaling medical events in a journal database.

FIG. 8A illustrates an embodiment of a process 800A for journaling medical events in a journal database. In one embodiment, the process 800A may be implemented by any of the MMS's described above (e.g., the MMS 620 or 720). In particular, the process 800A may be implemented by the journal management module 725. Alternatively, at least some of the blocks may be implemented by the journal modules 736, 746. Advantageously, in certain embodiments, the process 800A facilitates the generation of reports based on the journaled data.

At block 802, medical events are journaled in a journal database. In response to requests for report from a user (e.g., a clinician), at block 804 statistics about the medical events are obtained from the journal database. The statistics may include the type, frequency, and duration of medical events, the identity of clinicians or patients associated with the events, alarm response times, combinations of the same, and the like.

A report is generated at block 806 regarding the medical event statistics. At block 808, the report is used to identify potential areas of improvement in hospital operations. For example, the report can be a "monitoring report card" that assigns scores to the hospital or clinicians of the hospital based on their performance.

Figure 8B:
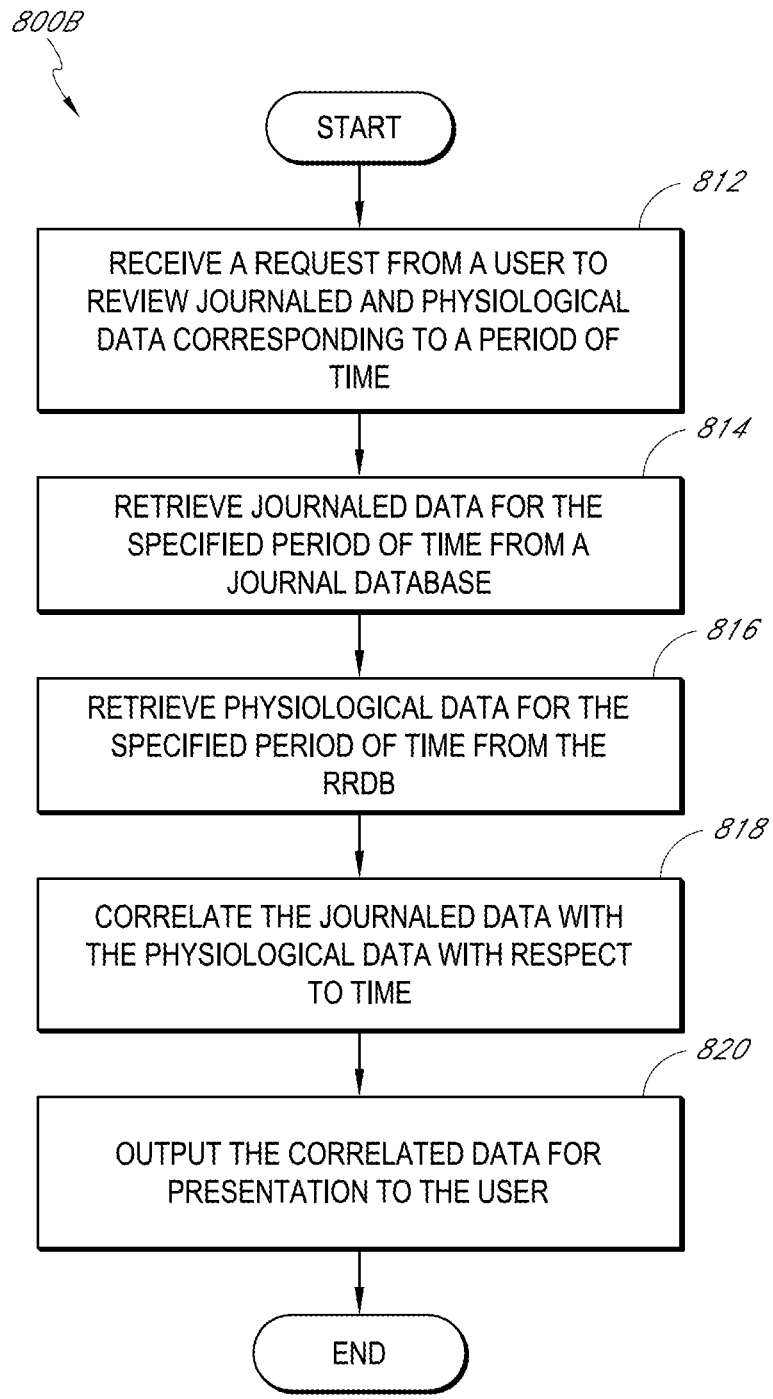
FIG. 8B is a flow chart illustrating an embodiment of a process for correlating data from the journal database and the round-robin database.

FIG. 8B illustrates an embodiment of a process 800B for correlating data from a journal database and an RRDB. In one embodiment, the process 800B may be implemented by any of the MMS's described above (e.g., the MMS 620 or 720). In particular, the process 800B may be implemented by the RRDB module 723 and journal management module 725. Alternatively, at least some of the blocks may be implemented by the RRDB module 744 and journal modules 736, 746. Advantageously, in certain embodiments, the process 800B enables physiological information from the RRDB and medical events to be correlated in time. Such a reconstruction of events and physiological data can be akin to aviation "black box" technology, allowing the user to replay clinical actions leading up to medical incidents.

At block 812, the request is received from a user to review journaled and physiological data corresponding to a period of time. The user may be a clinician, hospital administrator, or the like, who wishes to determine the cause of a problem in the healthcare of a patient. For instance, the user may wish to determine why clinicians failed to respond when a patient's $SpO_2$ dropped below safe levels.

At block 814, journaled data is retrieved for the specified period of time from a journal database. This block may be performed by the journal management module 725. At block 816, physiological data for the specified period of time is retrieved from an RRDB. This block may be performed by the RRDB management module 723. The journal data is correlated with the physiological data with respect to time at block 818. This correlation may include reconstructing a timeline of medical events, with values of physiological parameters (optionally including waveforms) provided in the correct time sequence on the timeline. In some embodiments, to facilitate this coordination between the RRDB management module 723 and the journal management module 725, timestamps in each database 722, 724 may be synchronized when the data is stored.

The correlated data is output for presentation to the user at block 820. The output may include, for example, a graphical view of medical events superimposed on physiological information (e.g., a waveform), or the like. Many display formats may be used for the correlated data.

Figure 9:
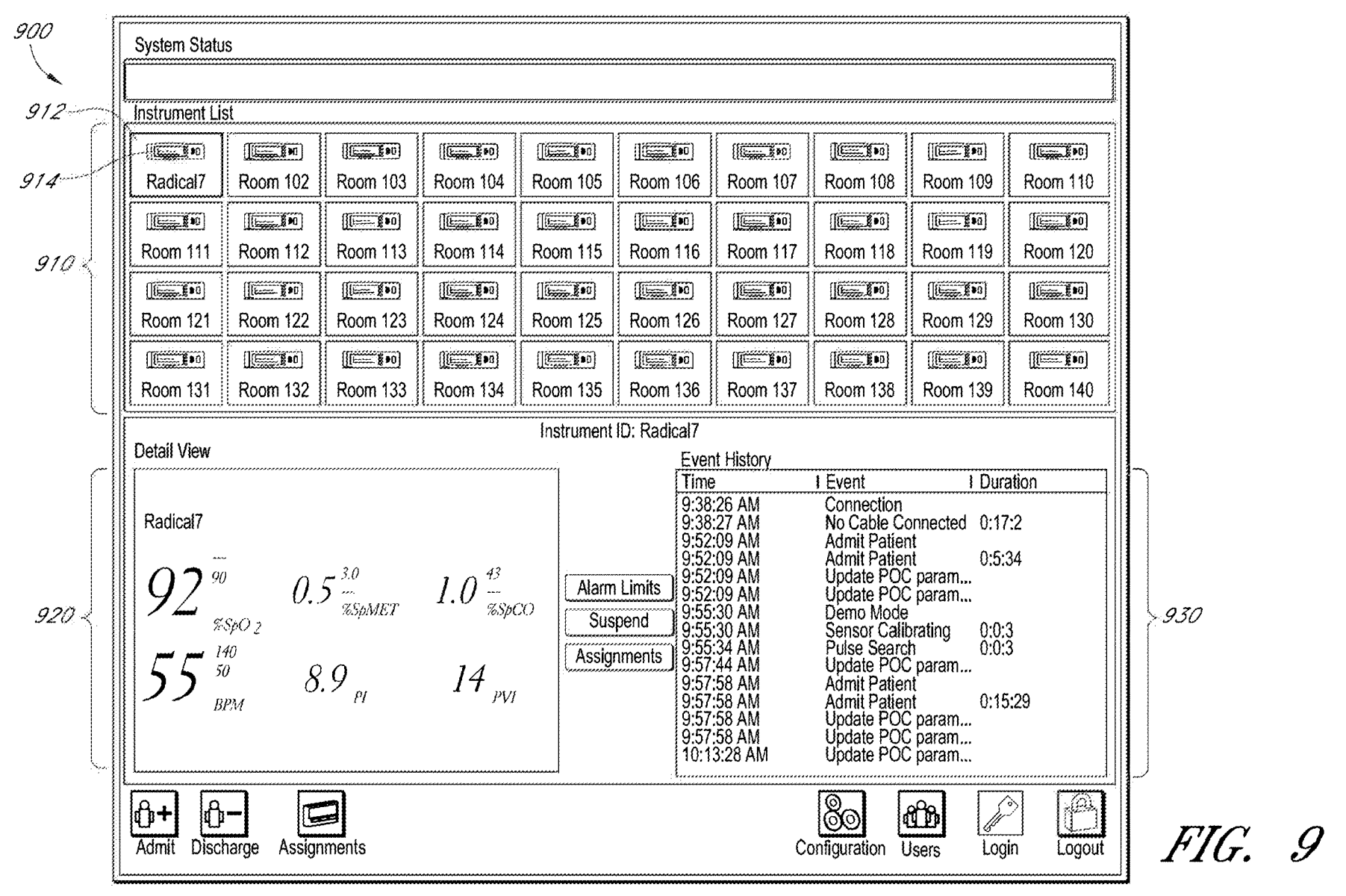

FIG. 9 illustrates an example graphical user interface (GUI) 900 for monitoring patients. The GUI 900 can be provided on a nurses' station system or the like. The GUI 900 can also be displayed on a clinician device.

The GUI 900 includes several display areas. In the depicted embodiment, the GUI 900 includes a patient status display area 910. The patient status display area 910 shows the status of multiple patients in a hospital or other clinical location. In an embodiment, patient status display area 910 depicts patient status for patients in a hospital department. Advantageously, in certain embodiments, the patient status display area 910 provides an "at-a-glance" view of multiple patients' health status.

The patient status display area 910 includes a plurality of patient status modules 912. Each patient status module 912 can correspond to a patient monitor that can be coupled to a medical patient. Each patient status module 912 can display a graphical status indicator 914. An example graphical status indicator 914 is shown in the screens 900 as a miniature patient monitor icon. The graphical status indicator 914 can selectively indicate one of several states of a patient monitor. In one embodiment, four possible patient monitor states can be depicted by the graphical status indicator 914. These include an alarm condition, a no alarm condition, patient context information status, and connection status.

In various implementations, the graphical status indicator 914 changes color, shape, or the like to indicate one of the different patient monitor states. For example, if an alarm condition is present, the graphical status indicator 914 could turn red to signify the alarm. If there is no context information available for the patient (see FIG. 1), then the graphical status indicator 914 could turn yellow. If the device is not connected to the patient or the network, then the graphical status indicator 914 could turn gray. And if there is no alarm condition, if there is context information, and if the patient monitor is connected to the patient and the network, then the graphical status indicator 914 could turn green. Many other colors, symbols, and/or shapes could be used in place of or in combination with the above-described embodiments.

Advantageously, the graphical status indicator 914 shows at a glance the status of a patient monitor. Thus, in the patient status display area 910, several graphical status indicators 914 corresponding to several patients show an at-a-glance view for the patient monitors corresponding to these patients. A clinician can therefore readily see the needs that a patient might have with regards to alarms, connection status, and context information.

Currently available graphical user interfaces for nurses' station computers tend to show a plurality of wave forms or changing physiological parameter numbers for each patient. This method of displaying patient information can be cluttered, confusing, and even hypnotic in some situations. Nurses working on a night shift, for instance, may find it difficult to concentrate on an alarm when several other patients' indicators on the display have changing numbers, changing waveforms, or the like. In contrast, in the graphical interface herein described, when the graphical status indicator 914 indicates an alarm condition, this alarm condition can stand out and be immediately recognized by the clinician.

Moreover, the graphical status indicator 914 simplifies the first level of analysis that nurses tend to perform. In currently available devices, nurses often have to analyze waveforms at the nurses' station to determine the health status of a patient. However, using the screens 900, a nurse need not interpret any waveforms or changing parameters of the patient, but instead can rely on the graphical status indicator 914 that indicates the presence of an alarm.

In certain embodiments, the patient status modules 912 can be selected by a single mouse click or the like. Selecting a patient status module 912 in one embodiment can bring up a patient monitor view area 920. The patient monitor view area 920 shows a view of a patient monitor corresponding to a selected patient status module 912. In certain implementations, the patient monitor view area 920 can show a view of the screen from the actual patient monitor device at the bedside of the patient. Thus, a clinician can readily recognize the physiological parameters of the patient in a format that the clinician is likely familiar with. The patient monitor view area 920 is currently receiving physiological information from a patient.

A history view area 930 in certain implementations can show medical event data corresponding to a selected patient monitor status module 912. This medical event data can be obtained from a journal database for inclusion in the GUI 900. The historical view 930 can show, for example, when a sensor was connected or disconnected from a patient, when alarms were active, and when a patient was admitted to the hospital or department. Although not shown, the history view area 930 can also be configured to show trend data obtained from an RRDB instead of, or in addition to, the journaled data.

Patient Monitoring Device with Video Calling Functionality

Figure 10A:
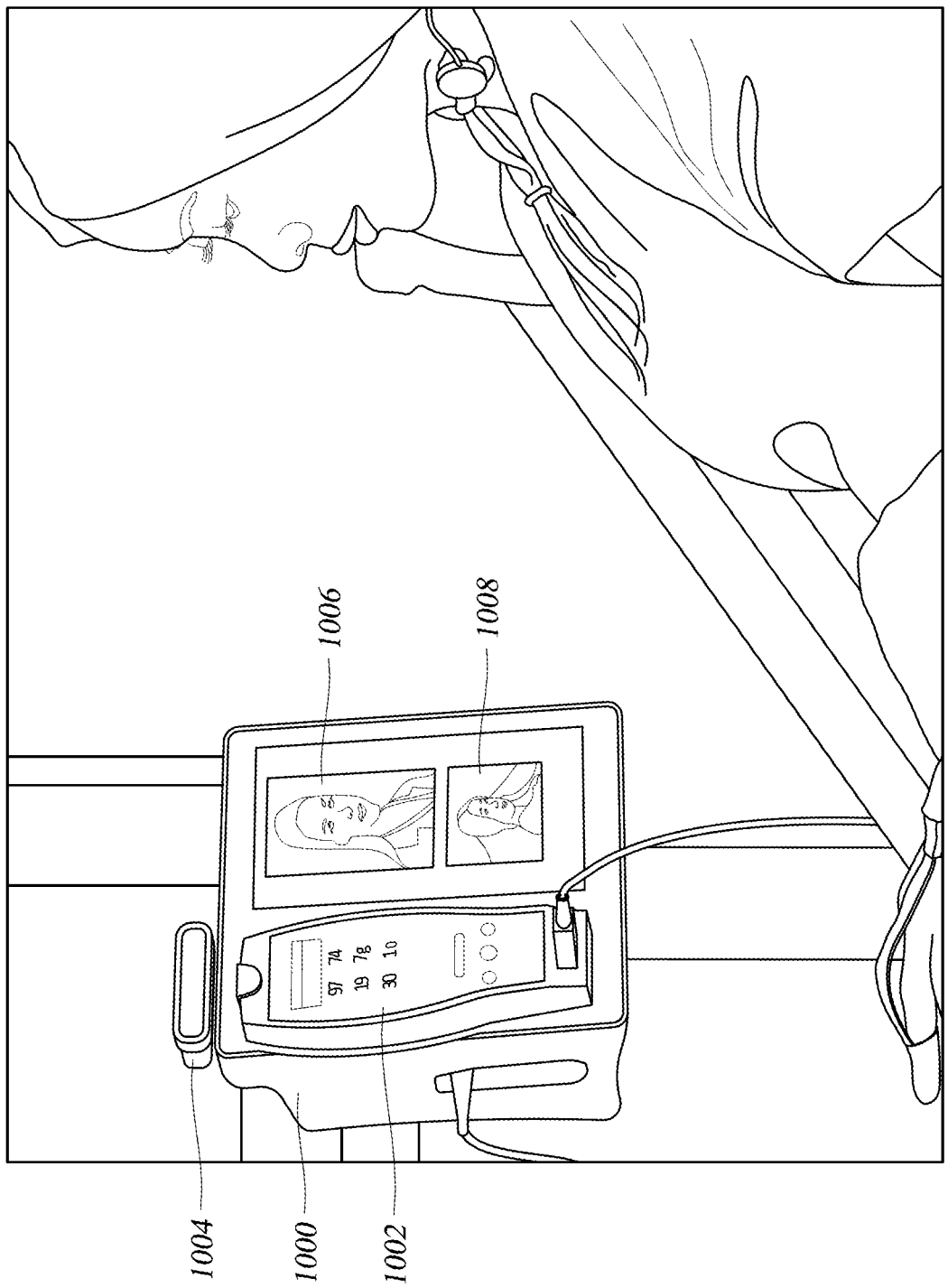
FIG. 10A illustrates an embodiment of a patient monitoring device with video calling functionality.

FIG. 10A illustrates an embodiment of a patient monitoring device 1000 with video calling functionality. The patient monitoring device 1000 can have any of the features described with respect to other patient monitoring devices herein. The patient monitoring device 1000 includes a physiological parameter display area 1002. The physiological parameter display area 1002 is used to graphically and/or numerically display measurements of one or more physiological parameters.

The patient monitoring device 1000 can also include a camera 1004. The camera 1004 is capable of capturing image data, such as still images and/or videos. The camera 1004 can also capture audio data. The camera 1004 may capture image data using visible and/or infrared light. Visible light capture may be advantageous during daylight hours, whereas infrared light capture may be advantageous during evening hours when the patient's room is dark. As illustrated, the camera 1004 can be mounted on top of the patient monitoring device 1000, though other mounting positions can also be used. In some embodiments, the camera 1004 may be integrated into the housing of the patient monitoring device 1000. The direction in which the camera 1004 is aimed can be adjustable, either manually or by remote control using one or more motors.

The image and/or audio data captured by the camera 1004 can be transmitted to a remote device using, for example, one or more communication networks, such as those described herein (e.g., computer networks such as LANs, WLANs, the Internet, etc., telephone networks, etc.). In some embodiments, one or more communication networks that are entirely or partially physically located in a hospital or other patient care center can be used. In some embodiments, external communication networks can be used to reach remote devices throughout the world. Thus, clinicians can remotely obtain a vast amount of information regarding the condition of their patients regardless of the clinician's location.

The patient monitoring device 1000 can be communicatively coupled with a remotely-located clinician camera. The clinician camera can capture image and/or audio data from a clinician and can communicate that data to the patient monitoring device 1000 using the same communication network(s) which is/are used to transmit image and/or audio data from the camera 1004 to the remote device being used by the clinician.

The patient monitoring device 1000 includes a clinician video call display area 1006 and a patient video call display area 1008. The image data from the clinician camera can be displayed in the clinician video call display area 1006. The patient monitoring device 1000 can also include a speaker to play the audio data from the clinician camera. Meanwhile, the patient video call display area 1008 can be used to display the image data being captured by the camera 1004. The patient video call display area 1008 may be advantageous in allowing the patient to adjust the aim of the camera 1004 and/or his or her own positioning with respect to the camera.

Figure 10B:
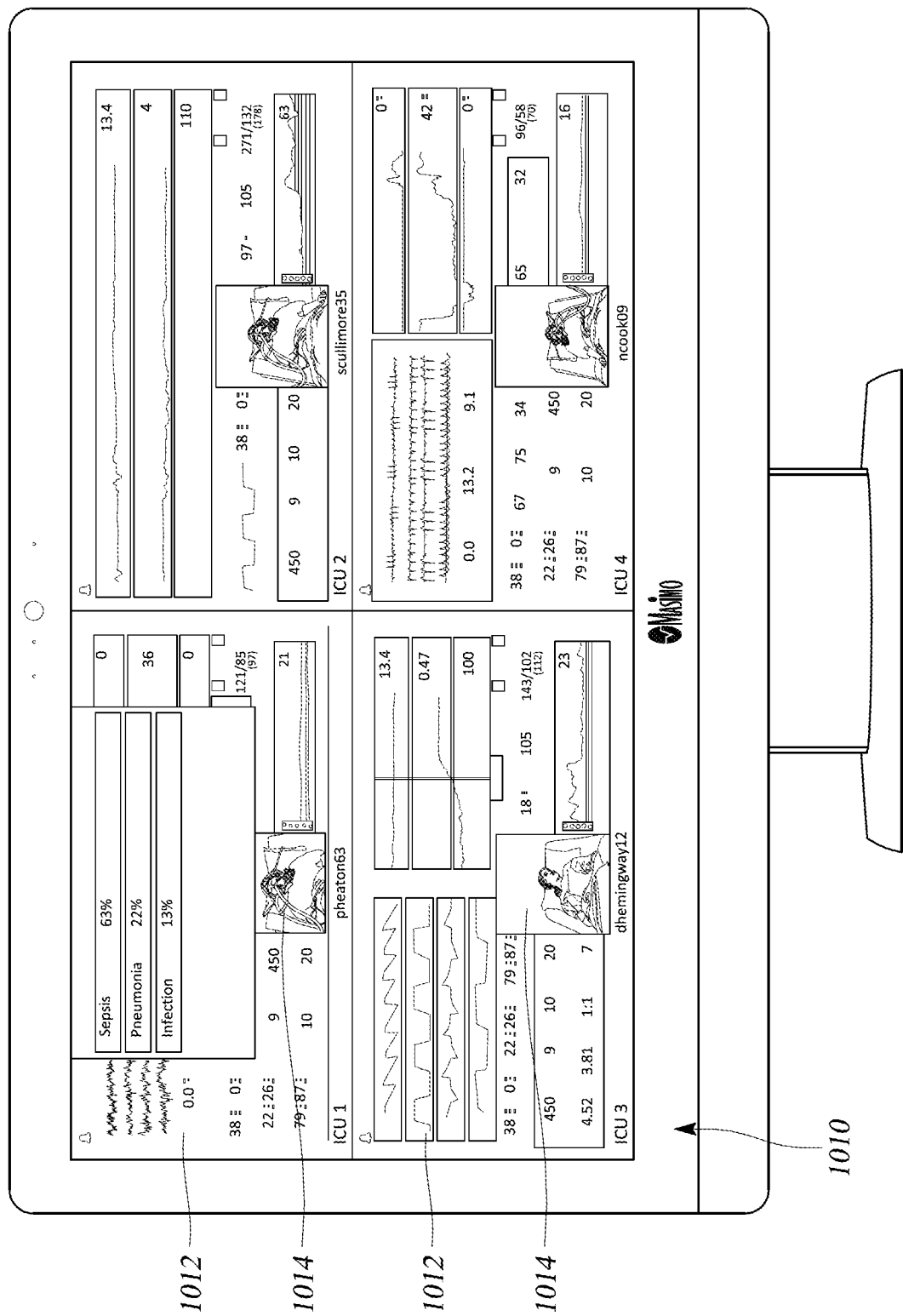
FIG. 10B illustrates an example embodiment of a graphical user interface (GUI) for monitoring a plurality of patients.

FIG. 10B illustrates an example embodiment of a graphical user interface (GUI) 1010 for monitoring a plurality of patients. The GUI 1010 can be provided on a nurses' station system or the like. The GUI 1010 can also be displayed on a clinician device. The GUI 1010 can have any feature described herein with respect to FIG. 9.

The GUI 1010 includes several display areas. In the depicted embodiment, the GUI 1010 includes a plurality of patient status modules 1012. Each patient status module 1012 can correspond to a patient monitoring device 1000 that can be coupled to a medical patient. Each patient status module 1012 can display graphical and/or numerical information about one or more physiological parameters. In addition, each patient status module 1012 can include a patient video display area 1014. Each patient video display area 1014 can display image data captured by the camera 1004 of the corresponding patient monitoring device 1000.

Patient Information System

Figure 11A:
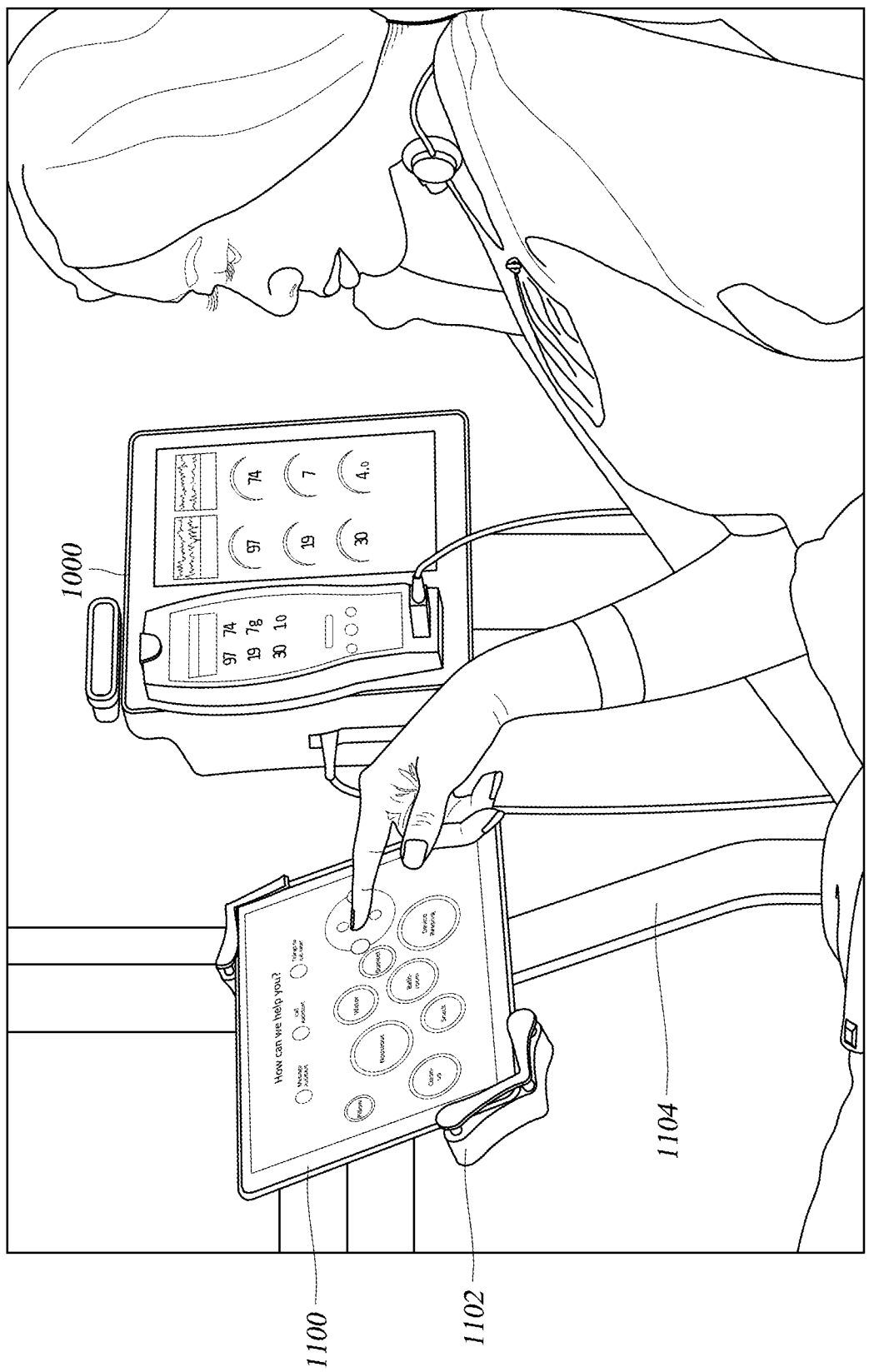
FIG. 11A illustrates an example embodiment of a patient information system.

FIG. 11A illustrates an example embodiment of a patient information system 1100. The patient information system can be used to provide a variety of features which are illustrated in FIGS. 11B-11J. The patient information system can include a display and an input device, such as a touchscreen, keyboard, mouse, etc. In some embodiments, the patient information system 1100 may be a tablet computer, a laptop computer, a smart phone, etc. The patient information system 1100 can be mounted to a patient's bed with one or more supports, such as the illustrated support arm 1104. The patient information system 1100 can be removably attached to the support arm 1104 by one or more releasable fasteners 1102. In some embodiments, the patient information system 1100 can also include a communications interface to communicatively couple the patient information system with a patient monitoring device 1000 by a wired or wireless connection. In addition, the patient monitoring device 1100 can be communicatively coupled with one or more communication networks.

Figure 11B:
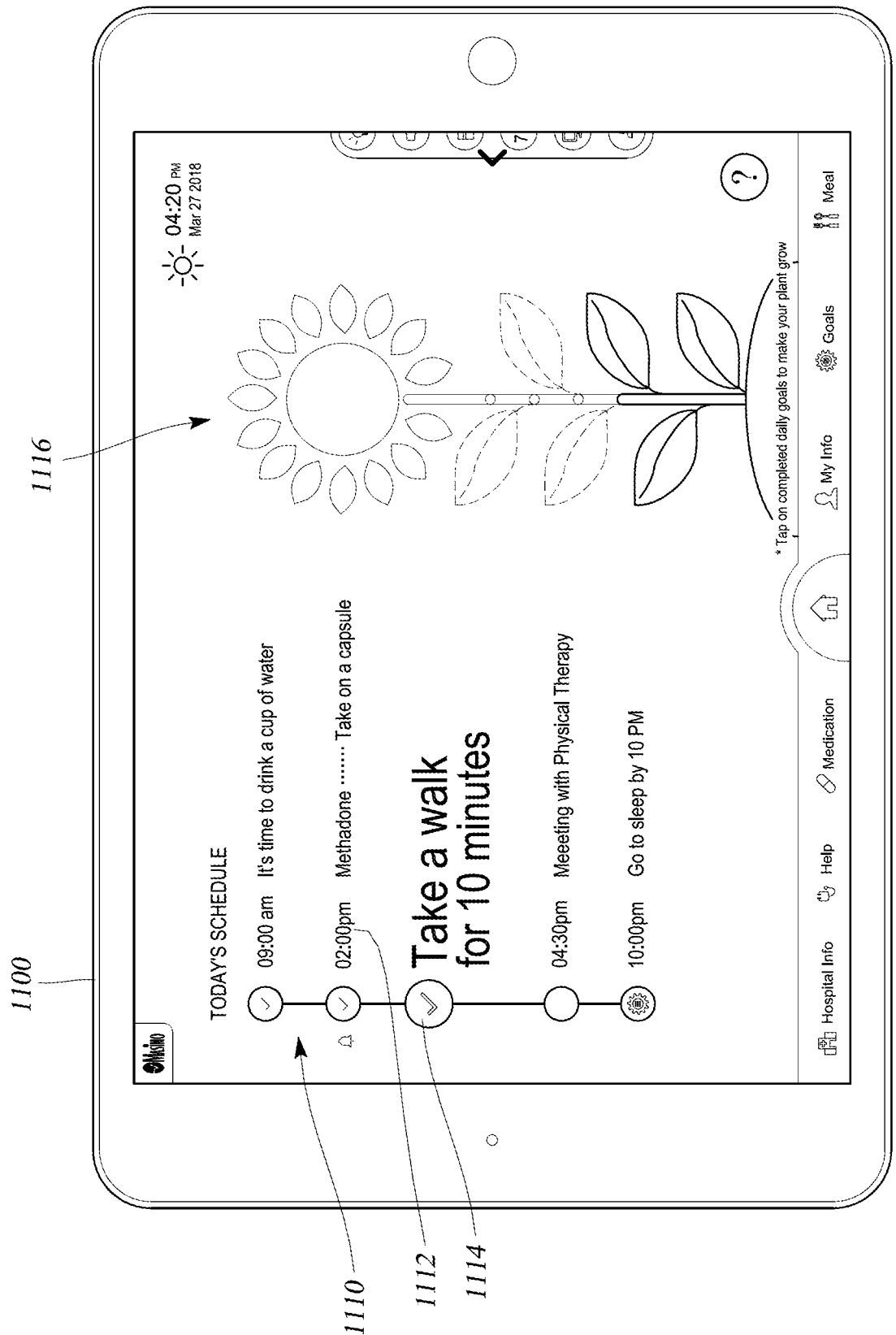
FIG. 11B illustrates an example embodiment of the patient information system of FIG. 11A which includes a schedule module.

FIG. 11B illustrates an example embodiment of the patient information system 1100 which includes a schedule module 1110. As illustrated, the schedule module 1110 can include one or more fields 1112 which display a listing (e.g., in chronological order) of the patient's appointments, tasks, goals, procedures, medication times, reminders, etc. for the day, week, month, etc. The schedule module 1110 can also include a compliance input region 1114 corresponding to each field 1112. The compliance input region 1114 can be used by the patient to indicate that he or she has complied with the item listed in the corresponding field 1112. In some embodiments, the compliance input region 1114 is a checkmark that can be toggled on and off.

In addition, the patient information system 1100 can include a schedule compliance indicator 1112. The schedule compliance indicator 1112 indicates, graphically and/or textually, the patient's compliance with his or her scheduled appointments, tasks, goals, procedures, medication times, reminders, etc. during the day. The schedule compliance indicator 1112 can provide an at-a-glance summary of how well the patient is complying with scheduled items. In the illustrated embodiment, the schedule compliance indicator 1112 is a graphical flower which the patient makes "grow" by indicating his or her compliance with scheduled items. For example, when the patient indicates, using the compliance input region 1114, compliance with a scheduled item, a leaf or petal can be displayed on the flower. The flower is but one example of a compliance indicator 1112; many other graphics can also be used.

Figure 11C:
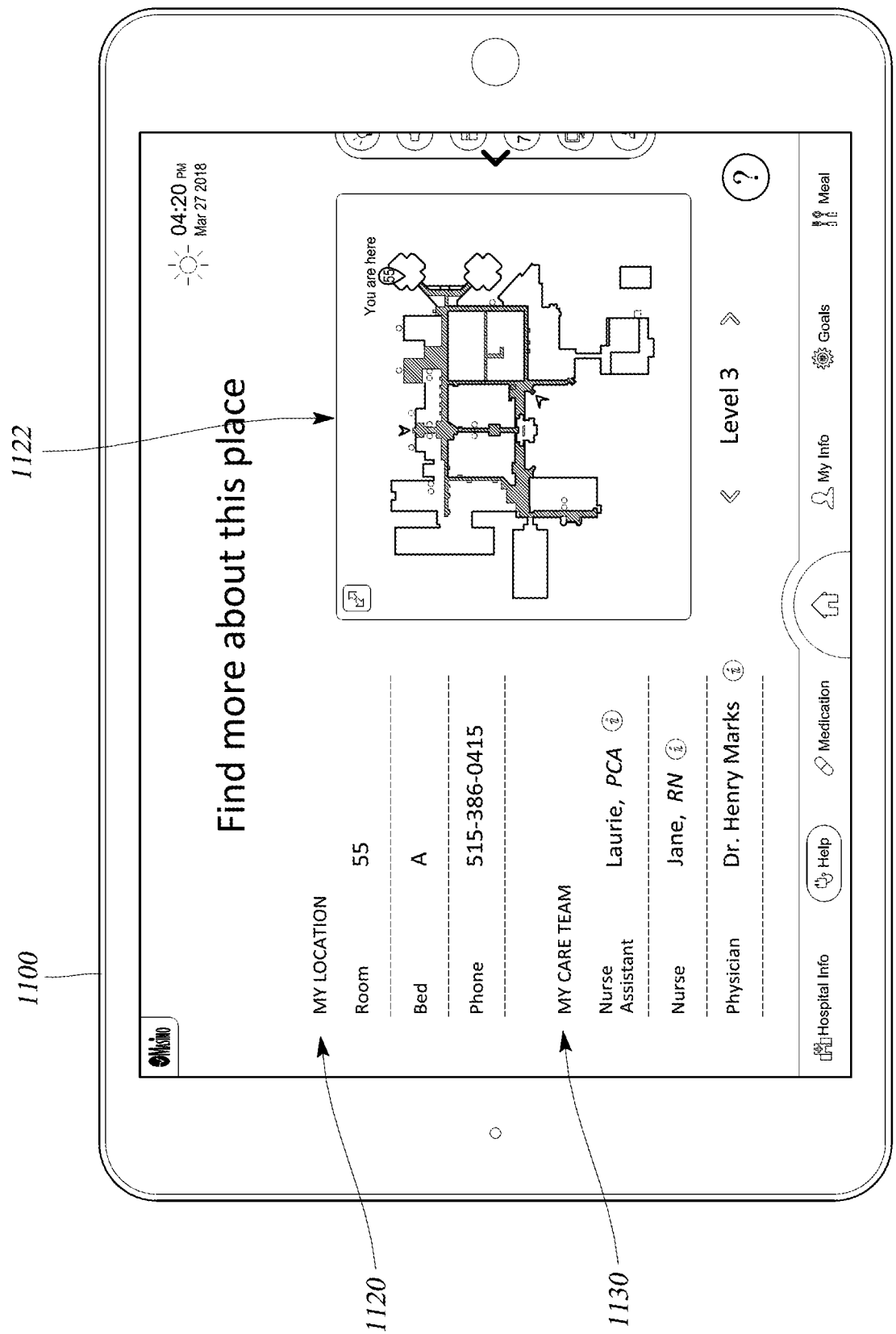
FIG. 11C illustrates an example embodiment of the patient information system of FIG. 11A which includes a location module, a map module, and an assigned clinician module.

FIG. 11C illustrates an example embodiment of the patient information system 1100 which includes a location module 1120, a map module 1122, and an assigned clinician module 1130. As illustrated, the location module 1120 can include one or more fields (e.g., room number, bed number, etc.) which indicate the patient's location. The location module 1120 can also include contact information, such as the phone number for the patient's assigned room. The location module can make it simple for the patient to access the required information to communicate with visitors and direct them to his or her room.

The patient information system 1100 can also include a map module 1122. The map module can show a map of the building where the patient is being cared for. The map module 1122 can also include an indicator that shows the location of the patient and/or the patient's room.

The patient information system 1100 can also include an assigned clinician module 1130. The assigned clinician module 1130 can include one or more fields which indicate the names and/or contact information for one or more clinicians assigned to care for the patient. The assigned clinician module 1130 can assist the patient in contacting his or her care team.

Figure 11D:
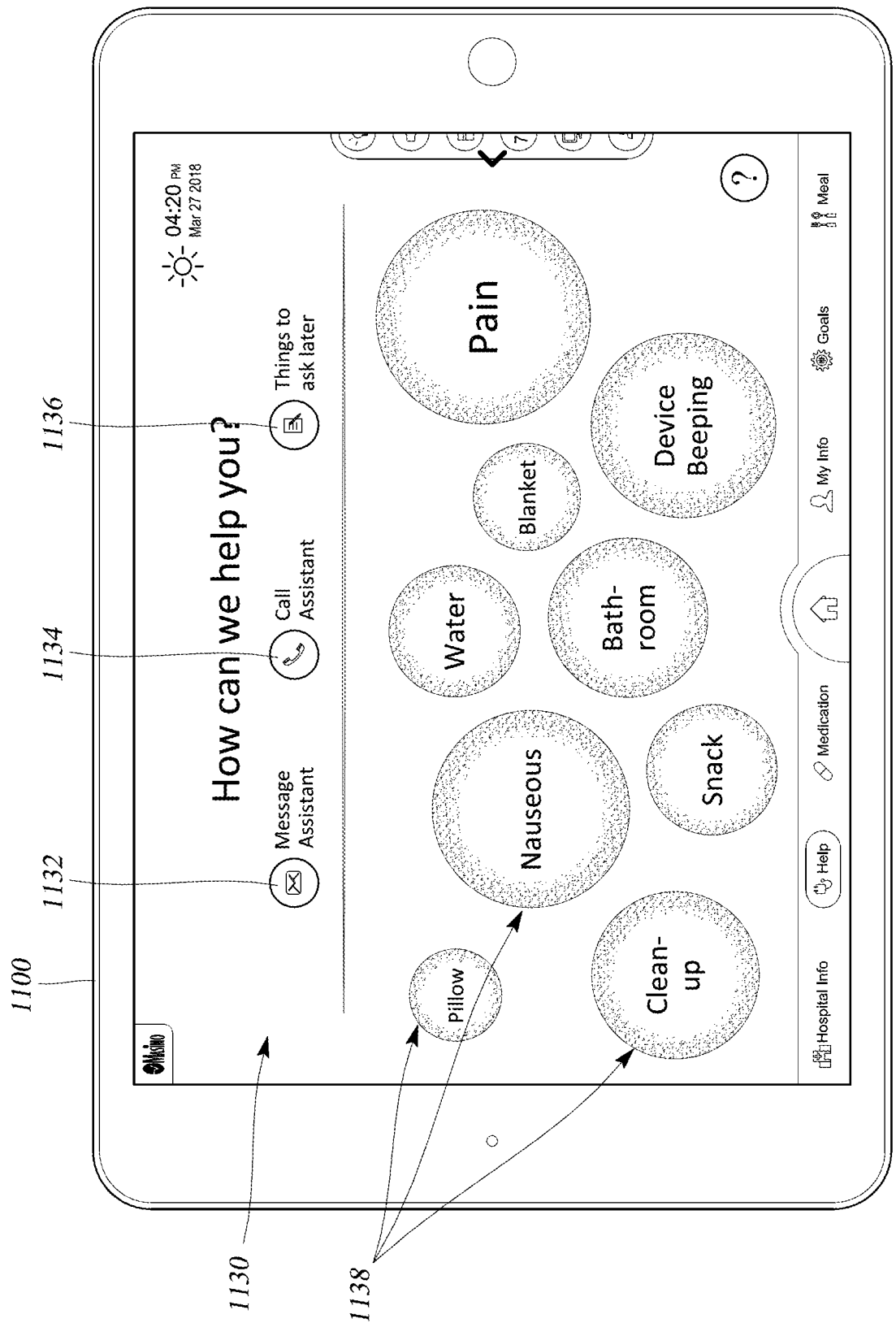
FIG. 11D illustrates an example embodiment of the patient information system of FIG. 11A which includes a communications module.

FIG. 11D illustrates an example embodiment of the patient information system 1100 which includes a communications module 1130. The communications module 1130 can include a messaging application 1132 for sending text messages to the patient's assigned care team. The communications module 1130 can also include a telephone or video call application 1134 for communicating with the patient's assigned care team by voice. In some embodiments, the telephone or video call application 1134 can invoke the video call functionality of the corresponding patient monitoring device 1000 shown in FIG. 10A. the patient information system 1100 can also include a question reminder module 1136. The question reminder module 1136 can allow the patient to input a list of questions to ask a clinician at a later time.

The communications module 1130 of the patient information system 1100 can also include one or more preset clinician notification inputs 1138. Each of the clinician notification inputs 1138 corresponds to a preset notification message. By interacting with one of the clinician notification input regions 1138, the patient can easily send a preset notification message to his or her assigned care team. Some examples of the particular notification messages include, for example, requests for a pillow, water, clean-up, a snack, a blanket, or other items. Some of the notification messages can also correspond to requests for pain medication, attention to a device in the patient's room which is beeping or otherwise indicating the need for attention, etc. In some embodiments, the visual prominence (e.g., size, brightness, etc.) of each clinician notification input 1138 on the screen of the patient information system 1100 can be set based on the frequency of its usage. For example, a clinician notification input 1138 that is used most frequently by the patient, or by a selected group of patients, can be displayed with the largest size. The clinician notification input 1138 with the next most frequent usage can be displayed with the next largest size, and so on. In this way, the patient can more easily access the most frequently used clinician notification inputs 1138. In some embodiments, the visual prominence (e.g., size, brightness, etc.) of each clinician notification input 1130 on the screen of the patient information system 1100 can be set based on its importance or criticality (e.g., as determined by hospital staff).

Figure 11E:
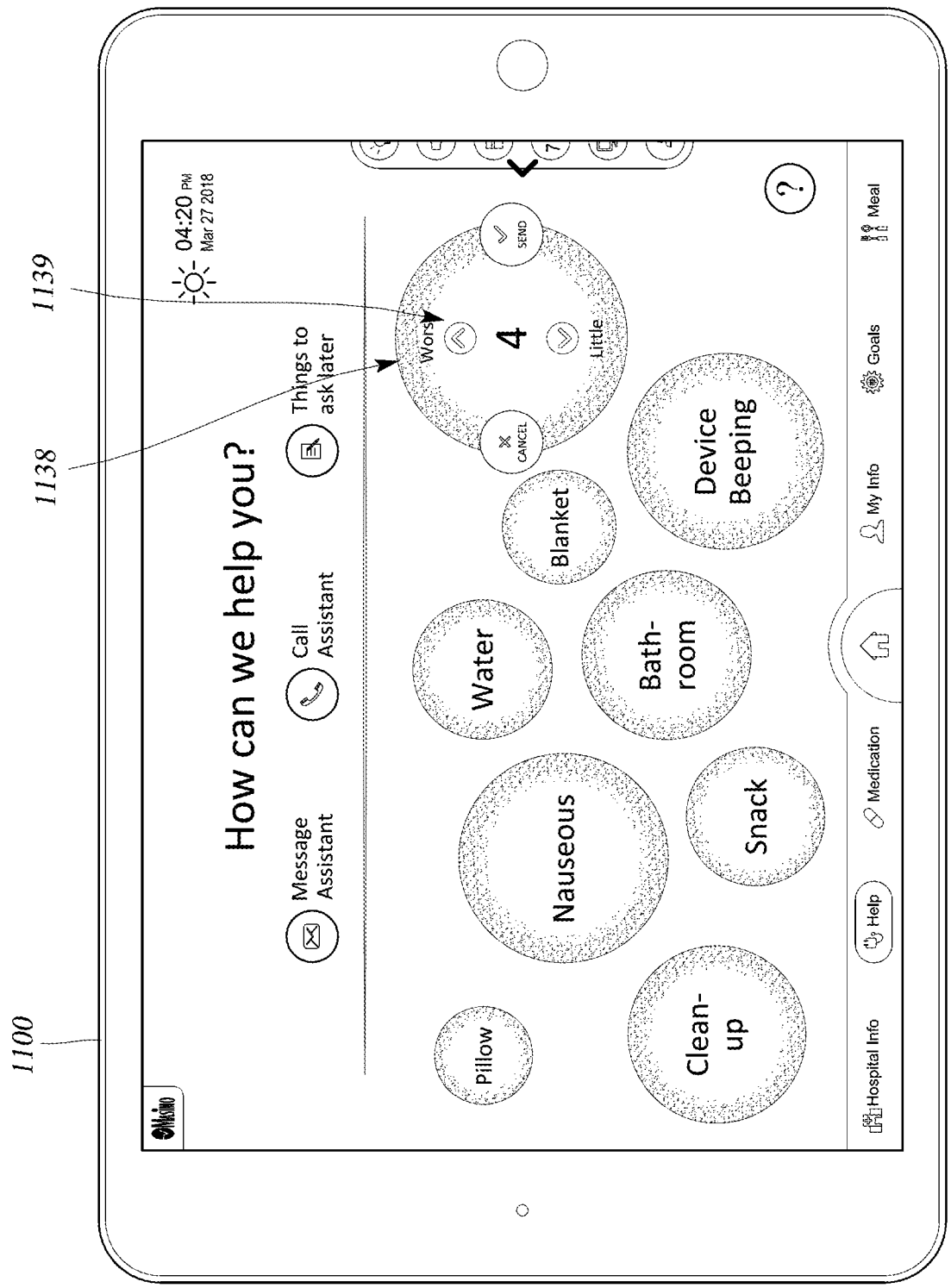
FIG. 11E illustrates an example embodiment of a preset clinician notification input after having been activated by a patient.

FIG. 11E illustrates an example embodiment of a preset clinician notification input 1138 after having been activated by a patient. As shown, the clinician notification input 1138 can include an associated value 1139 that can be set by the patient so as to personalize the preset notification message. In the illustrated embodiment, the associated value 1139 can be set by the patient to personalize the preset "pain" notification message.

Figure 11F:
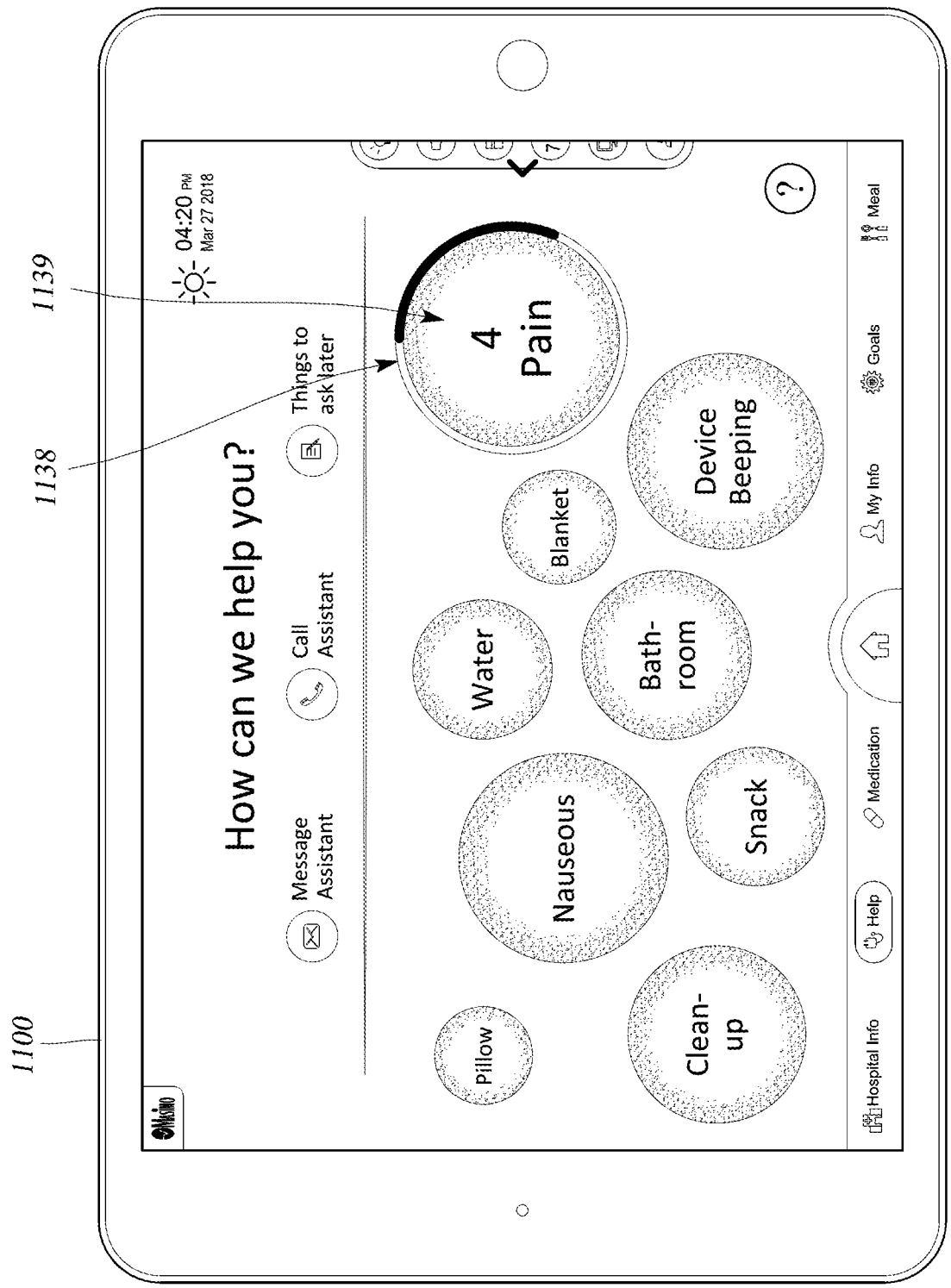
FIG. 11F illustrates an example embodiment of a preset clinician notification input after having been personalized by the patient.

FIG. 11F illustrates an example embodiment of a preset clinician notification input 1138 after having been personalized by the patient. In FIG. 11E, the patient personalized the preset "pain" notification message by selecting a pain level of "4." In response, the clinician notification input 1138 is updated with a graphic that corresponds to the selected value 1139. In the illustrated example, the graphic is highlighted arc around a portion of the perimeter of the clinician notification input 1139. The length of the highlighted arc is set so as to correspond with the selected value. Although the highlighted arc is one example of a graphic which can be added to the clinician notification input 1138 based on the selected value 1139, other graphics can also be used.

Figure 11G:
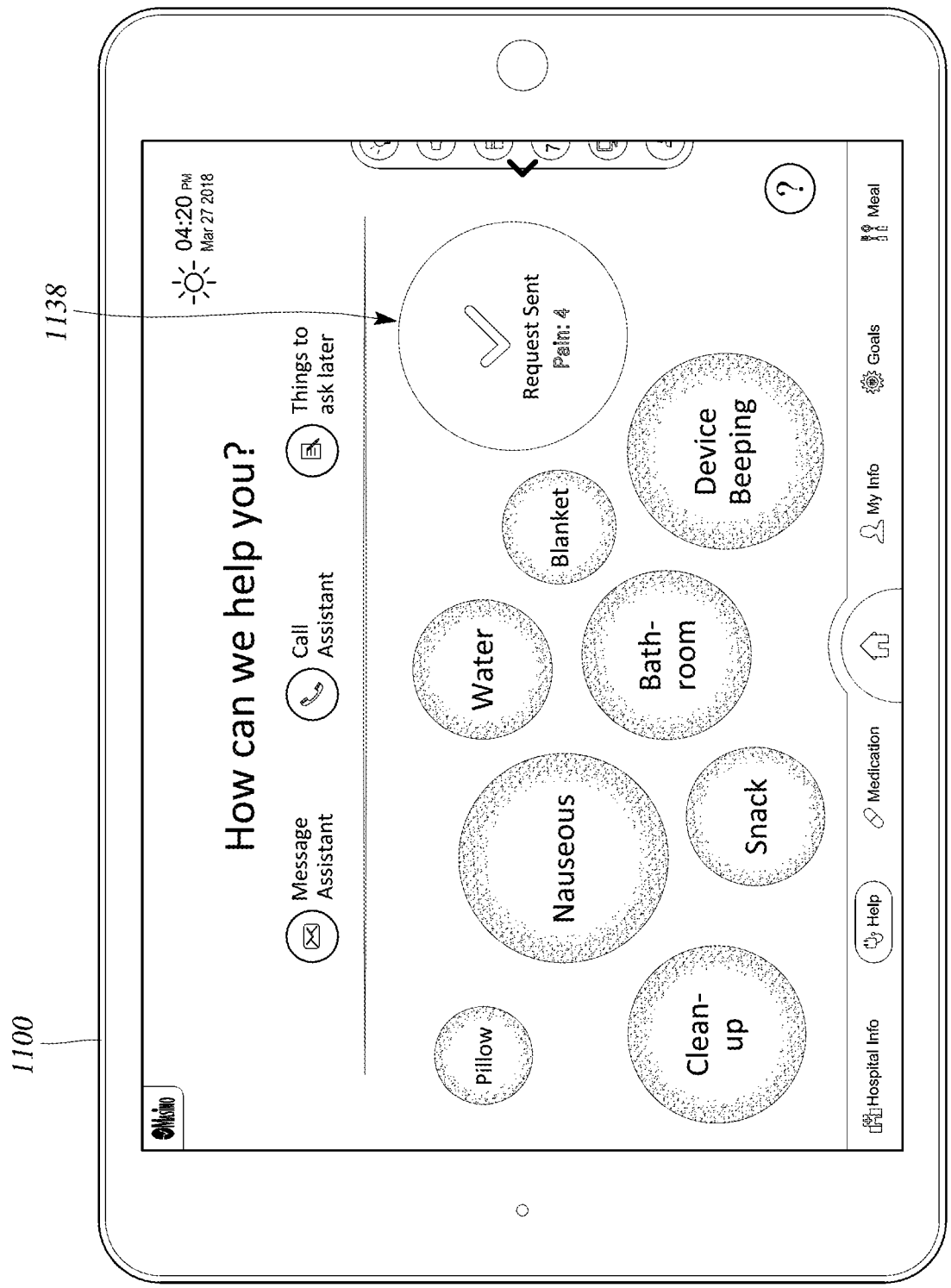
FIG. 11G illustrates an example embodiment of a preset clinician notification input after having been activated by a patient and after having successfully sent the corresponding preset notification message.

FIG. 11G illustrates an example embodiment of a preset clinician notification input 1138 after having been activated by a patient and after having successfully sent the corresponding preset notification message. In the illustrated embodiment, the "pain" clinician notification input 1138 can be updated with text and or a graphic to indicate that the patient's message has been successfully sent to his or her care team.

Figure 11H:
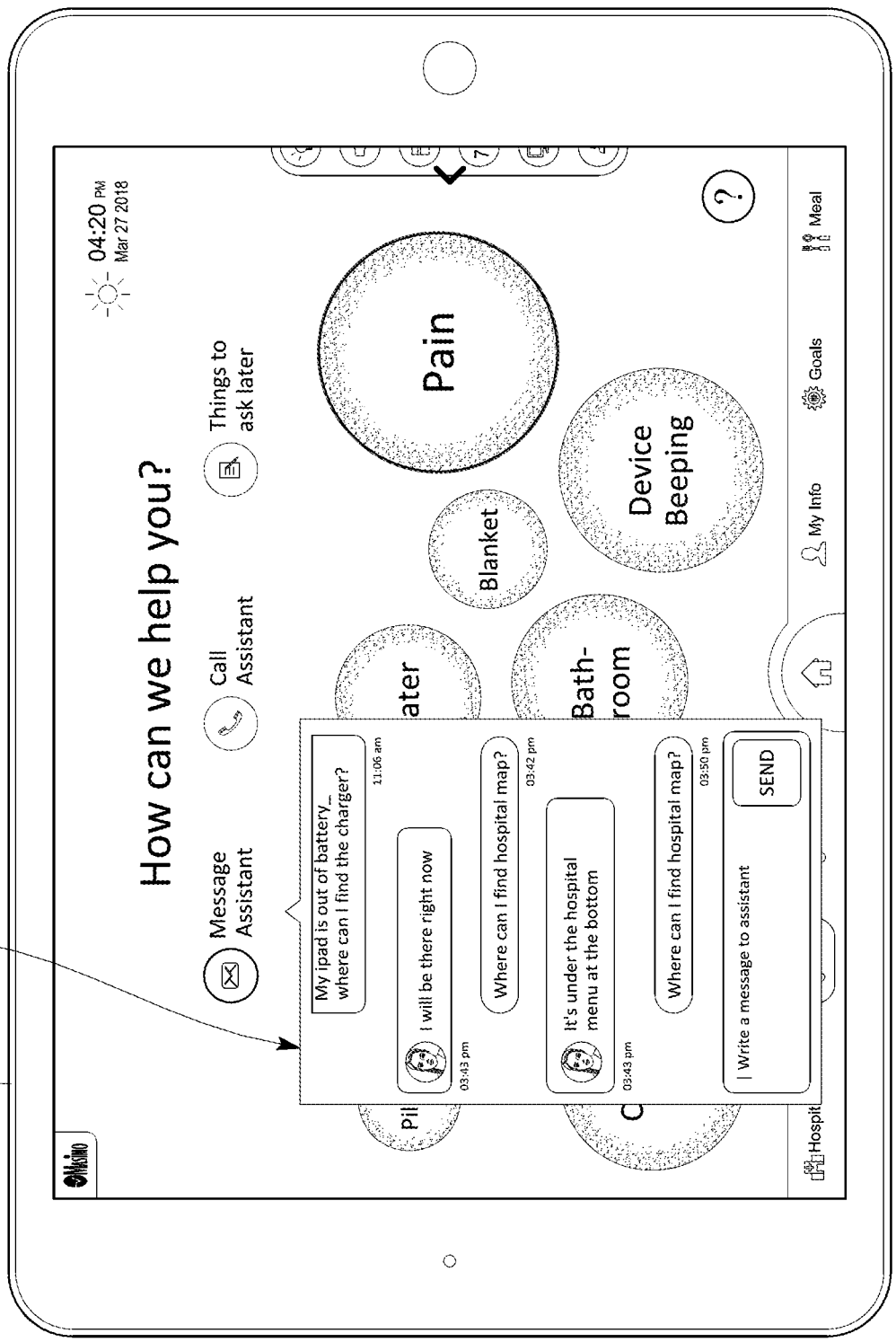
FIG. 11H illustrates an example embodiment of the messaging application of the patient information system of FIG. 11A.

FIG. 11H illustrates an example embodiment of the messaging application 1132 for the patient information system 1100. As shown, when a patient activates the messaging application 1132, a window appears to show a text message conversation between the patient and his or her care team.

Figure 11I:
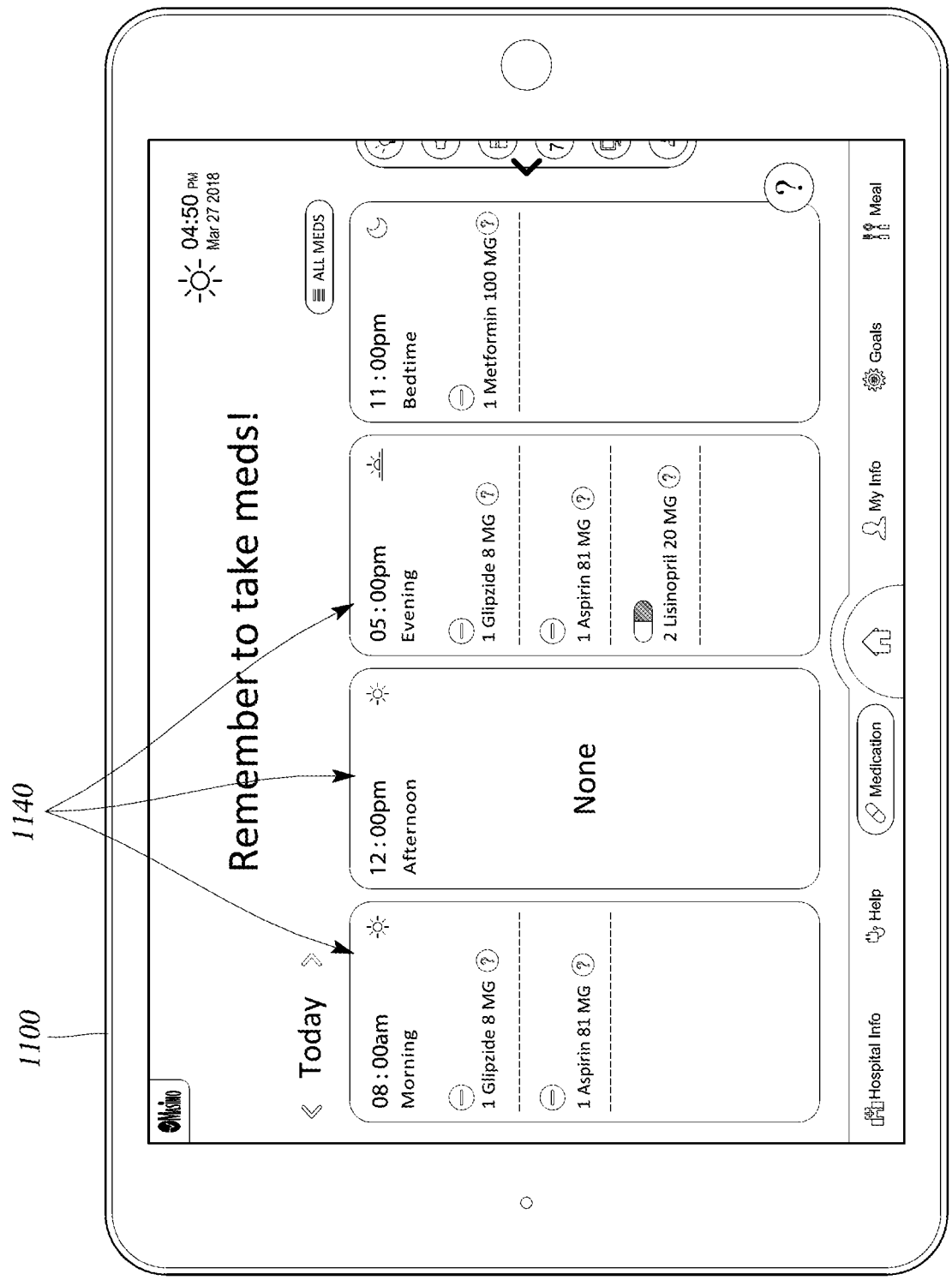
FIG. 11I illustrates an example embodiment of the patient information system of FIG. 11A which includes a medication schedule module.

FIG. 11I illustrates an example embodiment of the patient information system 1100 which includes a medication schedule module 1140. As illustrated, the medication schedule module 1140 can include one or more fields which display a listing (e.g., in chronological order) of the patient's medications, dosages, and/or times for the day, week, month, etc. The medication schedule module 1140 can also include fields to provide information about the medications, such as graphics which show what the medications look like, as well as usage directions, possible side effects, etc.

Figure 11J:
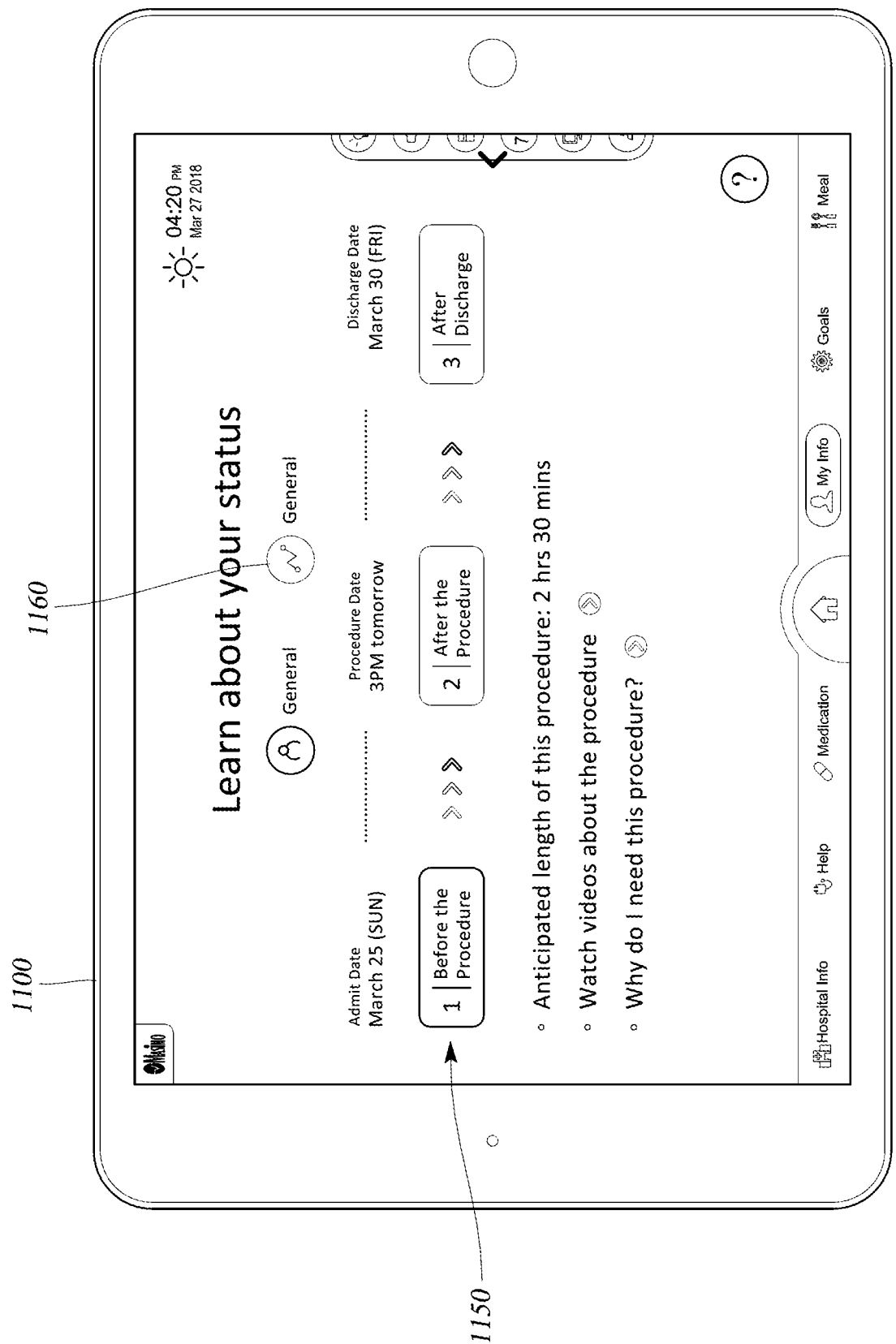
FIG. 11J illustrates an example embodiment of the patient information system of FIG. 11A which includes a medical procedure information module.

FIG. 11J illustrates an example embodiment of the patient information system 1100 which includes a medical procedure information module 1150. The medical procedure information module 1150 can include one or more fields which display a listing of the patient's scheduled medical procedures. The listing for each medical procedure can include the scheduled date and time of the procedure. It can also include the estimated duration of the medical procedure, a link to information (e.g., a video) which describes the procedure, instructions for preparing for the medical procedure, and an explanation of why the procedure is needed.

As illustrated, the patient information system 1100 can also include an input 1160 which the patient can select in order to display any or all of the vital sign information shown on the linked patient monitoring device 1000.

Figure 12A:
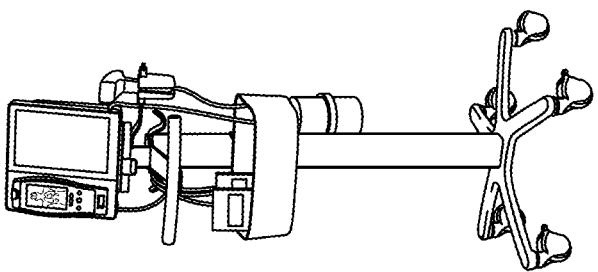
FIG. 12A illustrates an example embodiment of a mobile device application and method for remotely viewing a patient's vital signs and recording measurements to the patient's electronic medical record.
Figure 12A:
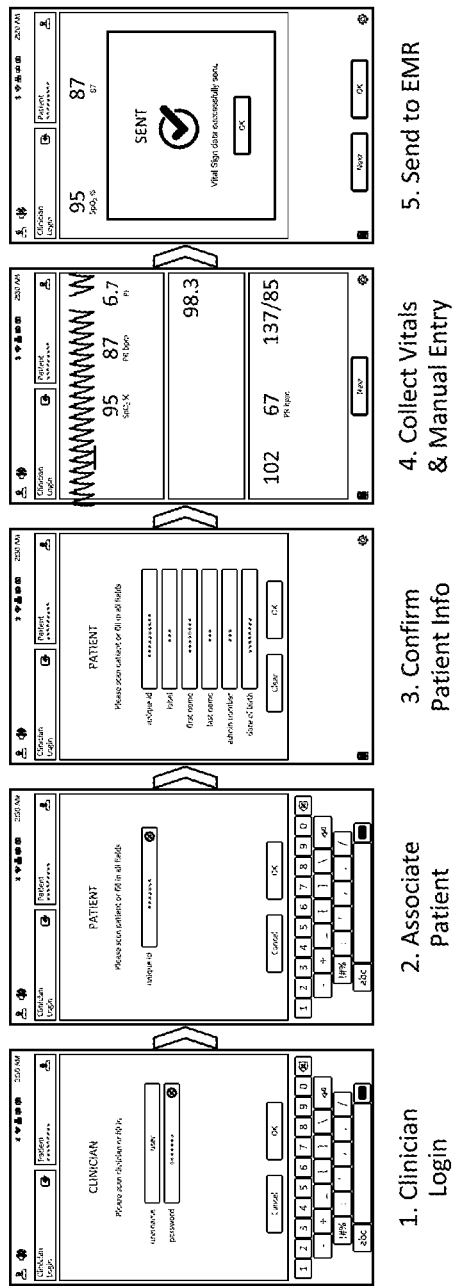

FIG. 12A illustrates an example embodiment of a mobile device application and method for remotely viewing a patient's vital signs and recording measurements to the patient's electronic medical record. During a login step, the application prompts the clinician to enter his or her name and password. During the next step, the application prompts the clinician to enter a unique identification for an associated patient. During the next step, the application prompts the clinician to confirm the patient's personal information, such as name, date of birth, etc. The application then receives one or more measurements from the patient monitoring device 1000 that is connected to the patient. The measurements can be displayed by the mobile application in graphical and/or text format. The mobile application can also include one or more fields for the clinician to enter vital sign measurements and/or additional clinical information. Finally, the mobile application includes can include a user input that allows the clinician to select and send one or more measurements, or other items of clinical information, to the patient's electronic medical record (EMR).

Figure 12B:
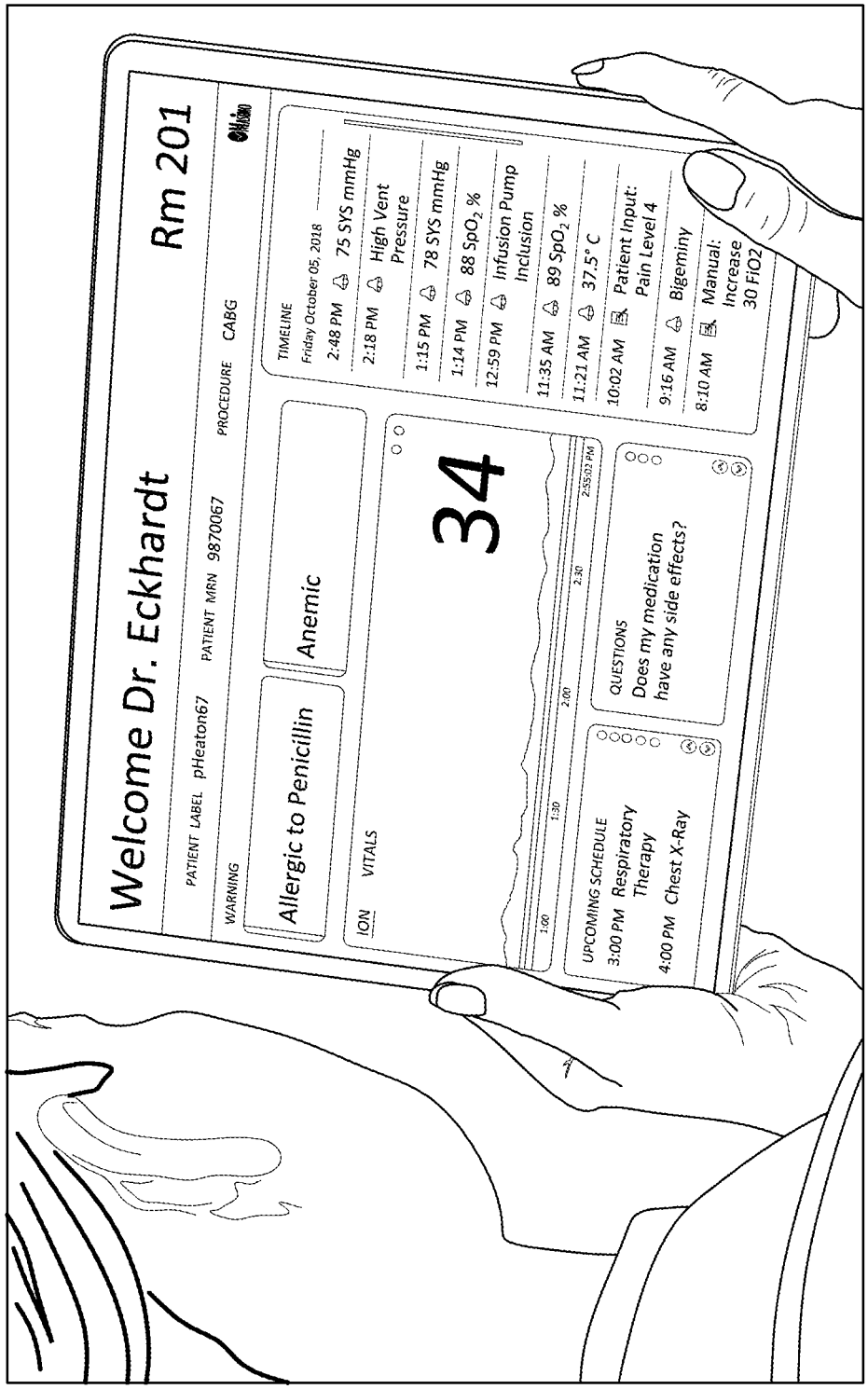
FIG. 12B illustrates an example embodiment of a mobile device application that allows a clinician to remotely receive, view, and send information to and from the patient monitoring device of FIG. 10A and the patient information system 1100 of FIG. 11A.

FIG. 12B illustrates an example embodiment of a mobile device application that allows a clinician to remotely receive, view, and send information to and from the patient monitoring device 1000 shown in FIG. 10A and the patient information system 1100 shown in FIG. 11A. The mobile device application connects to the patient monitoring device 1000 and to the patient information system 1100 via a network. The mobile device application then allows the clinician to receive communications (e.g., text messages, video calls, preset notifications, etc.) from the patient via the communications module 1130. The clinician can also view and edit the patient's schedule and medications via the schedule module 1110 and the medications schedule 1140. The clinician can provide medical procedure information via the medical procedure information module 1150. The clinician can also view monitoring data in real-time, as well as past data such as alerts, etc., from the patient monitoring device 1000.

Information and signals described herein can be represented using any of a variety of different technologies and techniques. For example, data, instructions, commands, information, signals, bits, symbols, and chips that can be referenced throughout the above description can be represented by voltages, currents, electromagnetic waves, magnetic fields or particles, optical fields or particles, or any combination thereof.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans can implement the described functionality in varying ways for each particular application, but such implementation decisions should not be interpreted as causing a departure from the scope of the present invention.

Depending on the embodiment, certain acts, events, or functions of any of the methods described herein can be performed in a different sequence, may be added, merged, or left out all together (e.g., not all described acts or events are necessary for the practice of the method). Moreover, in certain embodiments, acts or events may be performed concurrently, e.g., through multi-threaded processing, interrupt processing, or multiple processors, rather than sequentially.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, conventional processor, controller, microcontroller, state machine, etc. A processor can also be implemented as a combination of computing devices, e.g., a combination of a DSP and a microprocessor, a plurality of microprocessors, one or more microprocessors in conjunction with a DSP core, or any other such configuration. In addition, the term "processing" is a broad term meant to encompass several meanings including, for example, implementing program code, executing instructions, manipulating signals, filtering, performing arithmetic operations, and the like.

The steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, a DVD, or any other form of storage medium known in the art. A storage medium is coupled to the processor such that the processor can read information from, and write information to, the storage medium. In the alternative, the storage medium may be integral to the processor. The processor and the storage medium can reside in an ASIC. The ASIC can reside in a user terminal. In the alternative, the processor and the storage medium can reside as discrete components in a user terminal.

The modules can include, but are not limited to, any of the following: software or hardware components such as software object-oriented software components, class components and task components, processes, methods, functions, attributes, procedures, subroutines, segments of program code, drivers, firmware, microcode, circuitry, data, databases, data structures, tables, arrays, or variables.

In addition, although this invention has been disclosed in the context of certain preferred embodiments, it should be understood that certain advantages, features and aspects of the systems, devices, and methods may be realized in a variety of other embodiments. Additionally, it is contemplated that various aspects and features described herein can be practiced separately, combined together, or substituted for one another, and that a variety of combination and subcombinations of the features and aspects can be made and still fall within the scope of the invention. Furthermore, the systems and devices described above need not include all of the modules and functions described in the preferred embodiments.

What is claimed is:

1. A medical system comprising:
   a patient monitoring device configured to be coupled to a patient to monitor one or more physiological parameters;
   a patient information system; and
   a mobile application communicatively coupled with the patient monitoring device and the patient information system, and configured to allow a clinician to receive, view, and send information to or from the patient monitoring device and the patient information system,
   wherein the patient information system is configured to display the patient's schedule,
   wherein the patient information system includes one or more compliance inputs to allow the patient to indicate his or her compliance with a schedule item, and
   wherein the patient information system is configured to display a graphical schedule compliance indicator which indicates the patient's compliance with schedule items.

2. The medical system of claim 1, wherein the patient information system includes a communications application to allow the patient to communicate with the clinician by text or voice.

3. The medical system of claim 1, wherein the communications application includes a plurality of preset clinician notification inputs configured to send preset notifications to the clinician when activated by the patient.

4. The medical system of claim 3, wherein each of the plurality of preset clinician notification inputs is displayed with a visual prominence that corresponds to its usage frequency.

5. The medical system of claim 4, wherein the visual prominence corresponds to a displayed size of each of the plurality of preset clinician notification inputs.

6. The medical system of claim 4, wherein the usage frequency for each of the plurality of preset clinician notification inputs is determined based on usage by a selected group of patients.

7. The medical system of claim 3, wherein at least one of the preset clinician notification inputs is configured, when activated, to allow the patient to enter a value to personalize the corresponding preset clinician notification.

8. The medical system of claim 1, wherein the patient monitoring device includes a camera to allow the patient to conduct a video call with the clinician.

9. The medical system of claim 1, wherein the patient information system is configured to display the patient's medications.

10. The medical system of claim 1, wherein the patient information system is configured to display one or more fields that list a scheduled procedure and information about the procedure.

11. The medical system of claim 1, wherein the patient information system is configured to display a map of the patient's surroundings.

12. The medical system of claim 1, wherein the patient information system is configured to display contact information for one or more clinicians assigned to care for the patient.

13. The medical system of claim 1, wherein the patient information system is configured to display the one or more physiological parameters from the patient monitoring device.

14. The medical system of claim 1, wherein the graphical schedule compliance indicator comprises an image of an object that can be displayed in any of a plurality of states of completion, and wherein the patient information system is configured to display the image of the object to the patient in an advanced state of completion after the patient indicates his or her compliance with the schedule item.

15. The medical system of claim 14, wherein the patient information system is configured to display the image of the object in the most advanced state of completion after the patient has indicated his or her complete compliance with the schedule.

16. The medical system of claim 1, wherein the graphical schedule compliance indicator comprises an image with a plurality of sub-portions, and wherein the patient information system is configured to display the image to the patient with one or more of the plurality of sub-portions added to the image after the patient indicates his or her compliance with the schedule item.

17. The medical system of claim 16, wherein the patient information system is configured to display the completed image, with all sub-portions, after the patient has indicated his or her complete compliance with the schedule.

* * * * *